United States Patent [19]
Parker

[11] Patent Number: 5,460,055
[45] Date of Patent: Oct. 24, 1995

[54] SAMPLING METERING AND TRANSFER VALVE ASSEMBLY AND ANALYZING SYSTEM EMPLOYING SAME

[75] Inventor: Bernard Parker, Key Biscayne, Fla.

[73] Assignee: Coulter Corporation, Miami, Fla.

[21] Appl. No.: 178,719

[22] Filed: Jan. 10, 1994

Related U.S. Application Data

[63] Continuation of Ser. No. 796,278, Nov. 22, 1991, abandoned.

[51] Int. Cl.⁶ ................................................. G01N 1/14
[52] U.S. Cl. ............................................... 73/863.73
[58] Field of Search ....................... 73/863.71, 863.73, 73/863.83, 863.84; 422/103; 251/85

[56] References Cited

U.S. PATENT DOCUMENTS

| | | | |
|---|---|---|---|
| 3,567,389 | 3/1971 | Coulter et al. | 422/103 |
| 3,681,998 | 8/1972 | Karas et al. | 73/863.73 |
| 3,948,104 | 4/1976 | Stephens | 73/863.84 |
| 4,152,391 | 5/1979 | Cabrera | 422/103 |
| 4,521,225 | 6/1985 | Jenkins et al. | 73/863.73 |
| 4,756,201 | 7/1988 | Uffenheimer | 73/864.83 |
| 4,948,565 | 8/1990 | Bemis et al. | 73/863.73 |

FOREIGN PATENT DOCUMENTS

| | | | |
|---|---|---|---|
| 0218861 | 9/1987 | Japan | 73/863.73 |

Primary Examiner—R. Raevis

[57] ABSTRACT

A multifunctional liquid sampling, metering and transfer valve assembly and the analytical system employing same. The valve assembly is capable of performing all liquid handling functions therewithin. The valve assembly comprises a pair of coaxially arranged valve discs engaged in frictional, sealed face to face disposition and includes plural axially parallel through passageways arranged for selective communication, one disc being rotatable relative to the other. Plural dedicated flow paths are defined by said passageways for metering, storing and delivering precise volume aliquots of sample, of diluent and of lysing reagent (in respect of blood cell study) from sources of said liquids to mixing and/or testing chambers. Vacuum is employed to move the liquids along the dedicated flow paths aiding in preventing leakage from the junctions of the passageways within the valve assembly along the engaged surfaces. Further, the valve assembly is provided with a gimballed mounting coupling the assembly to a stepper motor, said mounting preventing vertorial misalignment of the discs (and passageways) during operation of the valve assembly. programmable control is provided so as to operate the valve assembly in accordance with a preset operational pattern.

32 Claims, 13 Drawing Sheets

SAMPLING METERING AND TRANSFER VALVE ASSEMBLY AND ANALYZING SYSTEM EMPLOYING SAME

CROSS-REFERENCE TO RELATED PATENTS

This application is a continuation of application Ser. No. 07/796,278 filed Nov. 22, 1991.

Reference is made to the following patents for their disclosures as examples of the prior art to the invention described hereinafter, each of said patents being incorporated by reference herein:

| U.S. Pat. No.: | Date | Patentee(s) |
| --- | --- | --- |
| 2,656,508 | October/1953 | Coulter |
| 3,549,799 | December/1970 | Rothermel et al |
| 3,567,390 | March/1971 | Rothermel |
| 4,152,391 | May/1979 | Cabrera |
| 4,445,391 | May/1984 | Cabrera |
| 4,507,977 | Apr/1985 | Cabrera |
| 4,896,456 | January/1990 | Cabrera et al |
| 4,957,008 | September/1990 | Proni et al |

Each of the above patents are owned by the assignee of the instant invention.

Reference also is made to the following patents, the disclosures thereof also being incorporated by reference herein:

| | | |
| --- | --- | --- |
| 3,583,232 | June, 1971 | Isreeli |
| 3,681,998 | August, 1972 | Karas |
| 3,489,911 | January, 1970 | Firman et al |

FIELD OF THE INVENTION

This invention relates generally to fluid metering and transfer valve assemblies. The invention is has considerable utility for use in a diluting system of the type wherein vessels, valves and connecting conduits are employed to measure, intermix, dilute and deliver fluids, particularly liquids, for the purpose of automatically making measurements and tests upon liquid samples for the medical, biological, chemical, industrial and allied fields.

Particularly, the herein invention provides a multiport, multifunction fluid sampling, metering, transfer, mixing and delivery valve assembly in which the primary fluid handling functions are performed by and within a single valve assembly, the fluid handling movements through the valve being effected by differential pressure, preferably by less than atmospheric pressure, which pulls the fluids, the moving discrete bodies of fluids being followed by air, primarily at atmospheric pressure.

The invention herein also is directed to provide means to constitute a solution to problems heretofore encountered with leakage and port alignment difficulties with the use of prior conventional valve assemblies used in the type of systems concerned herein whereby such leakage problems are eliminated and proper alignment of the ports is maintained throughout the operation of the valve assembly.

BACKGROUND OF THE INVENTION

Prior U.S. Pat. Nos., such as 3,567,390, 4,152,391, 4,445,391, 4,507,997 and 4,896,546, as well as 3,567,389, 3,991,055 and 4,702,889, provide examples of metering and transfer valve assemblies wherein internal measuring (metering) chambers are provided, generally in the form of passageways. In U.S. Pat. No. 3,567,390, a metering and transfer valve assembly is provided having a pair of outer disc members and a central disc member sandwiched therebetween, its opposite surfaces being frictionally engaged with the facing surfaces of the respective outer disc members. The discs are aligned axially and mounted on a spindle so that the outer discs are stationary while the center disc is rotatable between two positions. A pair of axially parallel measuring through passageway sets are provided in the central disc and matching passageways are provided so that in one position of the central disc, liquid sample is received within one measuring passageway of one set. The central disc is rotated to a second position where a precise volume of the liquid sample is isolated as an aliquot from the flow path of the said liquid sample and placed in communication with a second flow path. A precise predetermined volume of diluent is directed through the second flow path from a source exterior of the valve assembly. The sample aliquot is flushed from the valve assembly along with the predetermined volume of diluent and delivered to a mixing bath which carries electronic sensing means. After mixing, the mixture, now a precise dilution of the original liquid sample and comprising a diluted liquid suspension of the particles in said sample, is tested by passing same through the sensing means, same being a Coulter sensing aperture.

Simultaneous with the introduction of the liquid sample, a portion of the dilution is retrieved from the mixing bath and transferred to one measuring passageway of the second set of measuring passageways. When the central disc is rotated to isolate the aforementioned liquid sample aliquot, the "first" dilution is isolated in said one measuring passageway of said second set. When diluent is employed to flush a first dilution from the valve assembly, a predetermined precise known volume of diluent is employed to flush the measured portion of the prior made first dilution from the valve assembly to form a second dilution which is delivered to another testing location. The diluent volumes are premeasured exterior of the valve assembly and delivered to the valve assembly when needed. The testing is sequential per sample, the prior made "second dilution" being tested simultaneously with the testing of a current-made "first" dilution. Both sets of the segmenting passageways are formed in the central or rotatable disc of the valve assembly. Any reagents employed are introduced by means exterior of the valve assembly and delivered only into the mixing baths, never appearing within the valve assembly so as to avoid contamination of the flow paths within said assembly that are traversed by either the sample or the diluent.

A similar valve is provided in U.S. Pat. No. 3,567,389 with the use of spring means to maintain the valve elements in frictional sealed face to face engagement and wherein the spring means is relaxed slightly to permit rotation of one element relative the others for changing the relationship of the interior passageways defining one or another of the flow paths through the valve assembly. The tightened engagement of the facing surfaces was intended to avoid leakage during flow of the liquids along the flow paths..alignment likewise being maintained. Precise milling of the facing surfaces have been instituted with good effect to obtain a satisfactory sealed surface to surface engagement. Thus, Karas, U.S. Pat. No. 3,681,998, provided a hard, wear resistant surface for each of facing valve element surfaces with careful lapping of said surfaces to assure a leakproof seal therebetween. Even then, Karas also provided spring bias to maintain the said relationship. Nevertheless, such care in preparing the facing surfaces did not fully solve the problem since uneven wear resulted which limited the useful life of the valve assembly, necessitating service calls and likely early replacement of the valve assemblies. These valves also were not required to perform a multiplicity of functions, that is provision of measured samples were few and the necessary dilutions provided also were few. Not many flow paths were necessary and few passageways were required which had to be accommodated and aligned without interference ones with others.

Firman et al., U.S. Pat. No. 3,489,011 provided a slide liquid metering and transfer valve assembly formed of a pair of valve elements arranged one being slidable over the other, four pairs of ports being provided in the body and four cavities provided in the slide. Moving the slide from one position to a second position effected segmentation of a stream liquid from one pair of ports to transfer the segmented portion to a testing stream for analysis. In the embodiments therein disclosed, there were provided multiple chambers and multiple paths through which liquid flow was passed for segmentation, solvent being introduced to the segmented portions for transporting the combination to a destination. The valve assembly was limited to operation upon a flowing continuous stream of liquid or gaseous fluid, did not store the segmented portions as isolated portions, only delivered the segmented portions with accompanying solvent, i.e. used the solvent to propel the segmented portion from the valve assembly, did not provide for introduction to the valve of any corrosive or reactive reagent to pass therethrough, and provided no means to assure against misalignment or to prevent leakage from the passageway junctions of any liquid or gaseous fluid.

Isreeli et al, U.S. Pat. No. 3,583,232, did provide a "sampling" valve assembly formed of a pair of disc elements arranged coaxially in face to face engagement, one being a rotor and the other being a stator. The disc elements carried through passageways defining flow paths for passage of liquid sample, of a pilot fluid and air. A body of liquid sample was introduced and segmented into precise sample portions, loops were provided within which these portions were isolated and stored. However, only the sample liquid was metered and the pilot fluid was introduced to flush the isolated samples to a testing location. Air was introduced to separate the samples one from the others. No means was provided by Isreeli et al. to guard against or to prevent leakage from the internal passageway junctions, no other liquids were segmented to form metered volumes and stored within the valve assembly for delivery separate from the stored sample.

In U.S. Pat. No. 4,152,391, there is provided a metering and transfer valve assembly capable of forming three dilutions. This assembly comprises a pair of stationary disc members, stators, and a center, rotatable disc member, the rotor, sandwiched between the stators. The rotor carries one set of axially parallel, through segmenting passageways. A pair of external measuring loops are carried by the rotor, said loops passing through slots formed in one of the stators. The loops carry a precise volume of the liquid sample. One of the loops and the segmenting passageway of said one set are arranged to define a continuous flow path for the liquid sample during the loading of the valve assembly. The other loop is capable also of defining a continuous flow path with said segmenting passageway but the loops are parallel one relative to the other so that at least two aspirations, or loading steps, are required to provide the desired dilutions, alternatively.. The valve assembly also included internal gallery formations defining paths for communicating with selected passageways. Slots are necessarily formed in the stators in order to permit passage of the loops therethrough when the stators and rotor are arranged coaxially mounted on a shaft (or spindle) to enable rotation of the rotor relative to the stators for effecting the isolations of the precise sample volumes. Diluent for forming the dilutions is metered exterior of the valve assembly and introduced thereinto generally by means of pump operated dispensers.

U.S. Pat. No. 4,445,391 provided a liquid metering and transfer valve assembly wherein a measuring loop was secured to one of the stators in additional to the set of axially parallel segmenting passageways formed in the rotor. A series path was defined through the valve assembly including the loop and one of the set of segmenting passageways so that single loading step sufficed to fill both loop and segmenting passageway. With rotation of the rotor, a precise volume of liquid sample was isolated in said segmenting passageway and in said loop. An exteriorly metered volume of diluent was introduced respectively to the loop and to the said segmenting passageway to drive the isolated volumes of liquid sample, each with the known volume of diluent, to the testing location as respectively precise dilutions. The loop has only one function, that is, to meter the liquid sample volume. All other liquid volumes were measured exterior of the valve assembly and introduced as premeasured into the valve assembly. Reagents that were utilized as a part of the testing procedure were stored, measured and delivered from locations exterior of the valve, by-passing the valve assembly. Thus plural metering units, pumps, pinch and check valves, as well as considerable number of individual conduits, usually plastic tubing, were required resulting in complex arrangements and requiring considerable interior dedicated space, hence reducing the capable of achieving the compactness long sought.

U.S. Pat. No. 4,957,008 provided loop means for measuring and storing diluent, and for measuring small volumes of sample and storing same within axially parallel passageways within the valve assembly but the resulting assembly did not provide means for performing all of the fluid moving functions within the said assembly. No changes were provided for the facing surface to surface relationship to prevent leakage after a prolonged use. No provision was made for handling reagents such as lysing reagents within the valve, handling steps such as metering, storing and transporting such reagents within the valve assembly without contaminating other flow paths therewithin. Further, the number of functions required to be performed within the valve were less than those required to perform all functions expected of the system.

Surface to surface wear was not eliminated and though the useful life expectancy was satisfactory, improvements were nevertheless desired but not attainable. Positive means for preventing eventual leakage was not provided. It should be pointed out that the many prior art metering and transfer valve assemblies heretofore provided for the metering and transfer of precise volume liquid sample portions, particularly those for use in hematological studies and analyses, have not provided means for introducing corrosive reagents, such as lysing agents, into the valve assembly, metering precise volume portions and isolating same within said valve assembly and delivering said isolated portions from said valve assembly, after passing therethrough, to an exterior chamber for mixing with the blood samples delivered from the valve assembly.

When considering control, storage and transfer valve assemblies for use as means to control, meter, store and deliver precise and accurate quantities of fluids with a minimum of carryover, the valve elements have been assembled in face to face sealed, frictional engagement with the expectation that the fluids, ordinarily liquids, pass from flow paths in one element to selectively matched flow paths in the other valve element so that these fluids will flow across the junctions of said flow paths without leakage thereat, and, further, that the result will maintain the integrity of the fluids, particularly where these fluids are different. Accomplishment of such goal requires that the different fluids be maintained segregated ones from the others with no unintentional intermixtures. It has been found that such results or goals most often fail to be achieved.

It has been discovered that among the causes of such failure has been the forces generated by the translation of one valve element relative to the others during the operation of the valve assembly to place one set of flow paths in communication with another selected set of flow paths in controlling the flow through said valve assembly. Where there are many such translatory operations, avoidance of intermixtures of the respective fluids becomes critical, yet such avoidance has not yet been accomplished.

Applicant has recognized that such aforementioned forces tend to vary, however minimally, the relative disposition of the said engaged surfaces sufficiently to break the surfaces seals established between said surfaces, such disruption effecting the maintaining of the segregation of the fluids and result in cross-contamination effects. In addition to the possible cross-contamination effects, the fluids tend to pass along said surfaces, leaking from the valve assembly to the exterior thereof and escape into the surrounding environment. This is a significant hazard, particularly where the fluids are those which are hazardous to the environment and/or the operator(s). Exposure to such fluids, contact of the operator(s) therewith and/or contamination of the environment may be dangerous, such as would occur if the fluids are biological fluids and may contain communicable disease causal elements.

U.S. Pat. Nos. 2,656,508 and 3,549,994 describe some of the analytical systems of the general type employing fluid metering and transfer valve assemblies offered by certain ones of those described in the prior art reviewed above. These systems are capable of many uses in the medical, biological, chemical and allied fields, in research as well as routine testing and require means which can produce liquid mixtures of specific concentration accurately, repeatedly and automatically. Such systems are required to perform measurements on a continuous basis with many tests made simultaneously and complex routines repeated with precision but with different samples. Systems of the type described have been utilized to obtain a plurality of parameters of whole blood, for example, and include means for operating a plurality of valves, pumps, hydraulic circuits, sensing and analytical means whereby a whole blood sample is subtended to provide predetermined aliquots thereof of which respectively are directed to locations where they are diluted, lysed, measured and discharged. The requisite liquid samples must be drawn and precisely measured, combined with preselected volumes of diluent to define requisite precise dilutions thereof, the dilutions being transferred to vessels within the system which contain sensing means for generating signals, which, in turn, are directed to analyzing apparatus for determining the desired characteristic parameters sought. Often different degrees of dilution are required for determination of the different parameters of the original sample. Sample quantities often are limited and hence the multiple operations and deterinations preferably are performed utilizing a single liquid sample of relatively small volume. Conservation of sample is a desired goal. The number of fluids required, the distances required for the fluids to travel within the system, the complexity of the fluid circuits within the system, the necessity of providing plural pumps, pinch valves and fluid conduits within the system, all require a relatively large assemblage necessitating housing means of substance occupying considerable space.

Certain of the determinations require mixture of the sample with selected reagents, some of which may be corrosive in nature so that the sample, as well as any portion of the system, is protected from contamination by or exposure to such reagent. In addition, considerable care must be undertaken in handling of the liquids, particularly the corrosive reagents and the liquid samples, to avoid any dispersal thereof in the exterior environment adjacent the assemblage and to avoid contact of said sample with the person of the operator. Splashing, scattering or other dispersal of the sample or other contamination of the environment about the installation desirably must be avoided.

Leakage of sample and/or other liquids within or about the system should be greatly minimized, preferably eliminated. In such systems, the operations involved in providing the sample aliquots, the dilution of each sample aliquot respectively, and the transfer and delivery of said respective diluted sample aliquots to the sensing means of the system have been performed by metering and transfer valve assemblies offered by certain of the aforementioned United States patents.

It is highly desirable to retain valve integrity throughout the operation thereof, to provide a construction where the quantity of sample required to provide the necessity aliquots thereof can be significantly reduced, where air leakage into the valve assembly as well as accumulation of debris is avoided, where sample carryover is materially minimized, where the size of the assemblage also is reduced with attendant reduction of the space required by the assemblage comprising the system and where the versatility of the system considerably is increased, say by the elimination of the multiplicity of pumps, control valves, conduit and the like which are encountered in commercial units. Accordingly, it would be highly desirable but not yet available, to provide a valve assembly which is multi-functional, precise and accurate and is capable of performing the liquid handling within its confines.

Multifunctional valves generally require plural interior passageways in one valve element which are matched with selected cooperating passageways in another valve element, to define flow paths crossing the junctions of said respective passageways. Each of the flow paths are carefully related to the other flow paths and may be traveled by related or different liquids, for example. The more functions being performed by and/or within the valve assembly, the more distinct flow paths requiring more passageways are necessary. Not only must there be coordination of the valve elements so that proper passageways are aligned at the proper stage in the operation of the said valve assembly, the relative alignments at the passageway junctions must be exact, precision and accuracy of mating being critical. Precise relationships must be maintained, notwithstanding relative movement of the valve elements. This precision must be maintained over the useful life of the valve assembly, notwithstanding wear on the interior surfaces during use thereof.

Of further advantage, it would be desirable, but not as yet available, to provide a valve assembly that will operate with the entire system being a closed system, liquid being unable to escape the system to that a non-polluted environment can be provided with the protection of the integrity of the results, the atmosphere and the operating personnel.

It should be noted that apparatus embodying systems of the character heretofore available may range from the relatively early, less complex and relatively small units to large, most complex units requiring considerable dedicated space, as a greater number of parameters for determination are required with improvements, such as in medical and scientific knowledge and technology, are developed and more complex determinations and information must be obtained. Such apparatus share a common requirement for increased quantities of pumps, pinch valves, check valves, myriads of individual conduits for connections and cross-connections, manifolds, plural media storage containers, switching devices, etc., increasing the bulk of the apparatus, including its operational control, sensing, monitoring and data receiving and/or storage, analytical and delivery functional means.

Accordingly, the art has long sought apparatus of the character described which is a less complex nature yet which is capable of providing the many analytical functions which are provided by the use of the most highly complex and often bulky units available presently to the art. Reduction in size and complexity is a long sought after goal while retaining the precision, versatility, accuracy and reliability enjoyed with the more massive, highly complex units now available.

In addition, it would be desirable to provide a system of the character and purpose described which would possess increased versatility, would be capable of employment in a modular mode enabling operational coupling with a number of different modular operational units and results in an analyzing instrument which is compact, highly reliable, provides precise and accurate results, is easily serviced and maintained and is capable of being packaged as a materially reduced size unit as compared with prior instruments.

SUMMARY OF THE INVENTION

The invention provides a multifunction metering and transfer valve assembly for controlling and delivering precise quantities of fluids with a minimum of carryover, particularly useful for industrial control and instrumentation systems, said valve assembly being capable of effecting all liquid handling, including metering, storage and retrieval, transfer and delivery of the required volumes not only of liquid sample and of diluent, but also even of reactive reagent therewithin whereby obviating the prior necessity of providing the myriad pumps and control valves as well as materially reducing the number, length and complexity of conduit lines and networks that were required in prior systems and enabling the system to be closed so that liquid never escapes the system whereby to prevent polution of the environment in which the system operates.

The invention further provides a multiport, multi-functional sampling, metering, transfer and delivery valve assembly comprising a pair of coaxially arranged valve disc elements, one being a rotor and the other being a stator; said elements having plural through passageway sets opening to opposite faces thereof, said faces being lapped to a high degree of flatness and being frictionally engaged to establish a seal therebetween, means being provided to maintain said engagement and alignment yet permitting stepwise rotation one relative to the other with one engaged surface effectively tracking the other with limited freedom of movement, thereby preventing leakage and misalignment during operation of the assembly. In respect thereof, a balanced gimballed mounting is provided for the assembled pair of elements coupled to a stepper motor for driving the rotor and maintaining the engagement and alignment with the seal being maintained notwithstanding the possible uneven wear, wobbling, etc due to possible inclination of one valve element relative to the other(s) resulting from the rotary relative motion of the assembled valve elements.

The invention also provides a fluid valve assembly formed of at least a pair of valve elements having plural through passageways and facing surfaces arranged in frictional engagement and the surfaces defining surface seals one face relative to the other, whereby fluids being passed through selected ones of the through passageways are segregated, one of the valve elements being translatable relative to the other of the valve elements to place selected ones of the through passageways in communication with selected others of the through passageways while selected other ones of the through passageways are in non-communicating relationship and said valve elements being subject to forces tending to break the surface seals during relative motion of said valve elements, there being provided means causing one of the surfaces defining said surface seals to follow the movement of the other of said surfaces to preserve the surface seals intact whereby to maintain the segregation of the fluids passing through said valve assembly, the junctions of said passageways through which the fluids pass being maintained against misalignment which may result from said forces.

One advantageous feature of the aforementioned system is that it is a closed system, that is one where fluid cannot escape the system, and, where the primary motive force employed to effect the fluid handling functions is vacuum, that is, a reduced fluid pressure is the prime moving force effective for the performance of the required functions.

The valve assembly according to the invention advantageously functions for use in a blood analyzing system in that means are provided whereby lyse reagent can be introduced into said valve assembly, metered to define and to isolate therein a precise volume portion and to deliver that portion to a mixing and testing chamber, said means including defining a dedicated flow path whereby the lyse reagent fails to traverse any internal flow paths which may be traversed by blood sample or diluent.

The valve assembly according to the invention provides plural independent dedicated flow paths therewithin for different liquids and provides isolated storage therewithin for precise volumes of liquid sample, of diluent and for reagent for selective access thereto.

Another significant feature incorporated into the valve assembly of the invention is the internal arrangement whereby a source of reduced pressure is employed to move liquids through the valve assembly as the primary liquid moving means. In addition, all liquid handling is performed within the valve assembly according to the invention.

Further, the invention provides, in combination, a particle study system and the aforementioned valve assembly, said system comprising a small, compact, stand-alone assemblage formed of a group of cooperating subsystems including a diluting subsystem, a sensing subsystem coupled to the diluting subsystem and capable of developing and transmitting signals to an analyzing subsystem coupled thereto for determining and analyzing data from the signals directed thereto and delivering said analyzed data to a display subsystem coupled thereto. Additionally, a programmable control subsystem also is included for directing and coordinating the operation of said subsystems.

DESCRIPTION OF PREFERRED EMBODIMENTS

Figure 1:
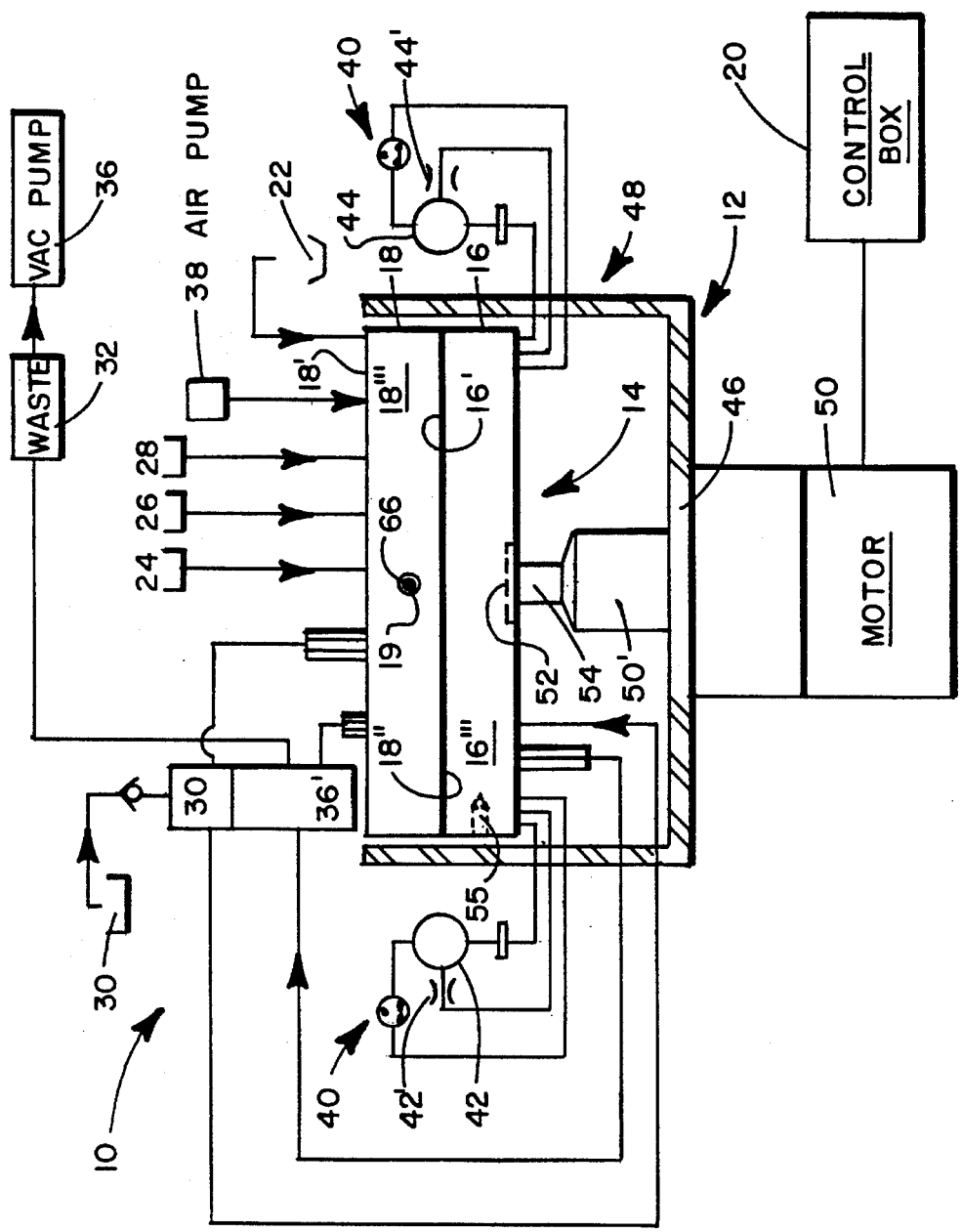
FIG. 1 is an elevational layout view of the invention as embodied in a particle study system, portions of said system being illustrated diagrammatically and illustrating the valve assembly as incorporated therein.

The particle study system provided by the invention hereinafter described is a closed system wherein liquid cannot escape the system whereby a non-polluting environment can be provided with protection of the integrity of the results, the atmosphere, the operating environment and the operating personel. The system features a sampling, metering, diluting, transfer and delivery valve assembly comprising a pair of valve disc members arranged coaxially superposed and arranged gimbal mounted to a stepper motor for step by step rotation of one element relative the other element.

The balanced gimballed mounting provided herein maintains the facing surfaces of the valve disc elements in frictional engagement and in alignment notwithstanding the rotary motion of one of the elements relative to the other. Vacuum preferably is the primary motive force employed to move fluids through the valve assembly with the trailing portions of said moving fluids being followed by air generally under atmospheric pressure as the trailing ports are open to air entry under the pulling influence of the vacuum source. The valve assembly is capable of effecting the entire fluid handling for the system. A programmable control means is provided for directing and coordinating the operation of the valve assembly and the particle study system hereinafter described.

Initially, the flow paths through the valve assembly, including all passageways, are occupied by air. The mixing and sensing means of the system are filled with isotonic diluent, as will be understood from the hereinafter description. The primary subsystem of the particle study system concerned herein is the diluting system, including the sampling, metering, storing, diluting, transfer and delivery valve assembly, said valve assembly including means for receiving a liquid sample to be tested in a single loading step from a source thereof and defining a single body of said sample along a first serial flow path within the valve assembly and including segmenting passageway means. The valve assembly is operable first to isolate at least a pair of sample aliquots, each of precise volume from said first flow path. Each sample aliquot is stored within the valve assembly for later delivery.

The valve assembly next is operated to receive diluent along a second serial flow path within the valve assembly. The valve assembly next is operated to isolate diluent aliquots from said second serial flow path, storing each for later delivery. The valve assembly is operated to receive the reagent component, here lysing reagent, along a third serial flow path within the valve assembly and thereafter, operated to define, isolate and store a reagent aliquot within said valve assembly for later delivery.

The valve assembly then is operated first to establish communication between the respective stored sample aliquots and respective diluent aliquots and deliver the respective sample and diluent aliquot to respective mixing and sensing means coupled to the valve assembly. The isolated reagent aliquot is introduced to one of the sample/diluent aliquot mixtures. The respective aliquots are mixed and then directed through the sensing means. The valve assembly is operated to rinse each of the flow paths through the valve assembly, replacing its contents with air, and to rinse the mixing and sensing means with diluent, making the system ready for the next following analysis.

As can be understood, considerable fluid handling is required for the operation of the system. The valve assembly provided by the invention is capable of undertaking most fluid handling, metering, storage, dilution, transfer and delivery operations as well as the other fluid movement operations utilizing negative fluid pressure, such as vacuum, from a source thereof provided as a component of said system, the negative fluid pressure preferably functioning as the primary motive force for moving the fluid bodies through the system, including the valve assembly and the mixing and sensing means.

In the ensuing description, the term "circulating passageways" is used to denote passageways in the valve assembly which link the measuring passageways to the delivery ports and facilitate movement of fluids, including liquids. The term "feed passageways" are defined as those passageways functioning as entry to liquids such as liquid sample, diluent, lysing reagent and/or cleaning liquids for introducing said liquids into the valve assembly.

Referring to the drawing, in FIG. 1 the system according to the invention can be described as a closed system designated generally by reference character 10 as a stand alone unit. The system 10 includes a support stand 12, a sampling, metering, storing, diluting, transfer valve assembly 14 and a balanced gimbal arrangement provided for mounting the valve assembly 14 on the stand 12 and coupling said valve assembly to the means provided to translate the rotatable element of the valve assembly. The stand 12 is represented diagrammatically in FIG. 1 by reference character 12, and in FIG. 22, by reference character 12'. The valve assembly 10 comprises a pair of like-dimensioned valve disc elements 16 and 18 of cylindrical configuration.

The valve disc elements 16 and 18 are coaxially superposed when assembled, the stationary element 18 over the rotary element 16. Valve disc element 16 is rotatable relative to the valve disc element 18, element 16 hereinafter referred to as the rotor 16 and element 18 being hereinafter referred to as the stator. The rotor 16 is provided with opposite surfaces 16', 16" and an outer circumferential surface 16'''; stator 18 having opposite surfaces 18', 18''' and outer circumferential surface 18'''. The facing surfaces 16" and 18" preferably are lapped to a high degree of flatness (for example, to within 2 Helium light bands (23.2 millionth of an inch) so that a seal is established therebetween to prevent passage of fluids along the said surfaces when the valve elements are engaged frictionally when assembled. The "seal" may be described as the resultant establishment formed of a plurality of surface seals.

A preferred embodiment of the valve assembly according to the invention is described as employed in a particle study system of the Coulter-type which provides data for the determination of selected parameters of a blood sample. In FIG. 1, a programmable control unit is represented diagrammatically by reference character 20 in FIG. 1. A source of blood sample is represented by reference character 22, a source of isotonic diluent for use in making the dilution utilized for RBC determinations is represented by reference character 24; a source of isotonic diluent for use in making the dilution used for WBC determinations is represented by reference character 26; and a source of lysing reagent also used for the WBC determinations is represented by reference character 28—all coupled to the stator by suitable conduit means. Other reagents and appropriate measuring means within the valve assembly can be employed additionally or alternatively. Also provided and coupled to the stator 18 is a source 30 of cleaner liquid. The source 30 is coupled to both the rotor 16 and stator 18. A waste receptacle 32 is provided to receive the liquids from the valve assembly 14 during the course of the operational cycle thereof. A vacuum source, such as vacuum pump 36, is coupled to vacuum manifold 36' and thence, to respective through passageways in the rotor and stator for supplying reduced pressure fluid to be applied to selected passageways of said valve assembly 14. A source of pressurized air, such as air pump 38, can be provided coupled to the valve assembly 10 so that pressure can be applied in lieu of or supplemental to the application of reduced pressure (less than atmospheric pressure or vacuum) from the vacuum source 36.

The mixing and sensing system 40 comprises a pair of mixing vessels 42 and 44, each coupled to the rotor 16, each vessel 42 and 44 functioning to receive the respective sample aliquots, diluent aliquots and the reagent aliquot required (if any) for performing the desired determinations. Sensing means in the form of Coulter-type sensing apertures are designated by reference characters 42' and 44', representing the sensing means respectively for the WBC and RBC determinations. Mixing is performed by introducing air, preferably in the form of bubbles, from the valve assembly 14 immediately following delivery of the respective aliquots to the respective vessels. Air is introduced to follow the content of the respective flow paths by applying vacuum to one port opening at one end of a flow path thereby drawing air into the valve assembly at the opposite end of said flow path, said opposite end being open to the atmosphere.

Figure 22:
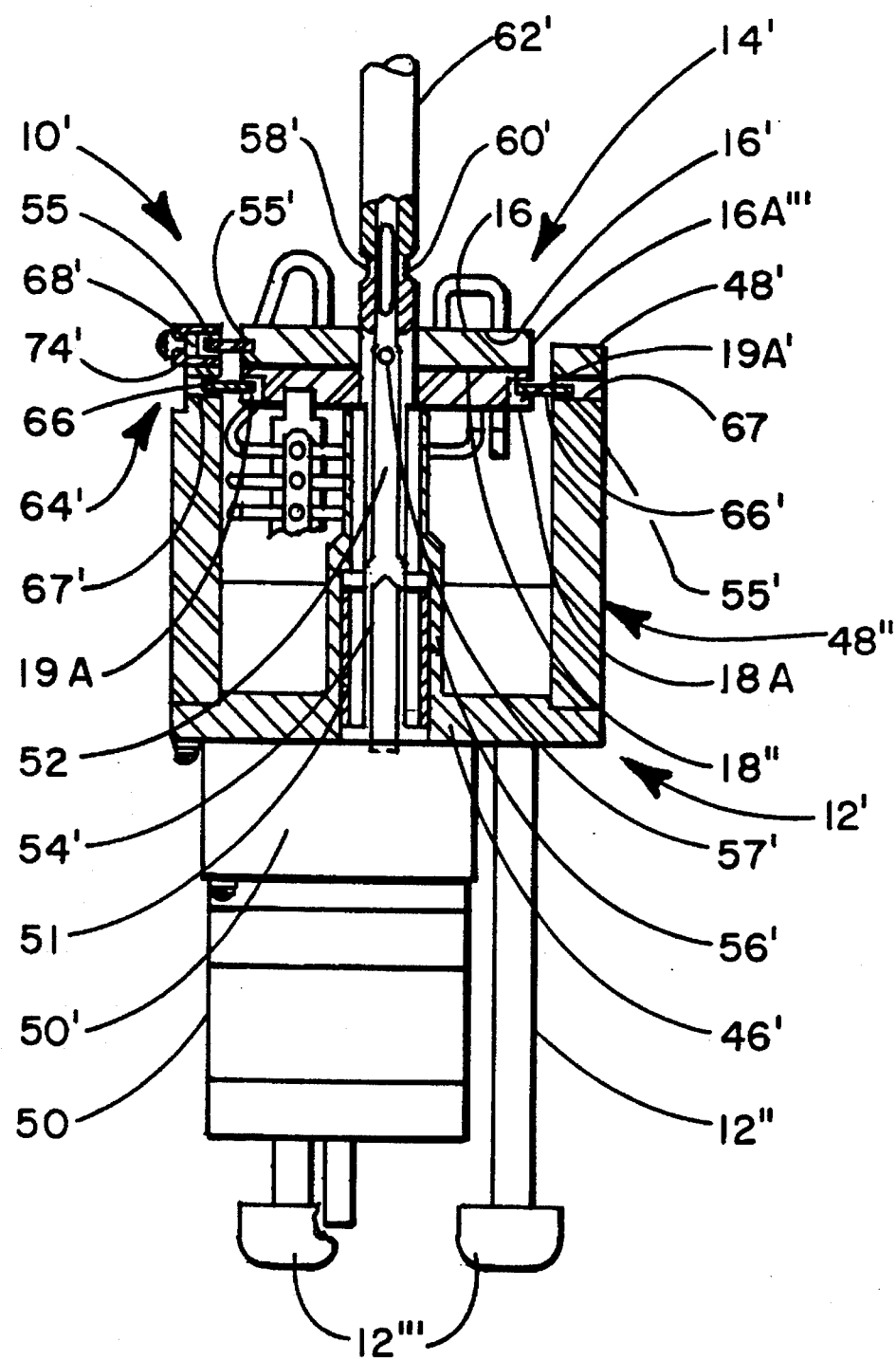

The stand 12 comprises a base plate 46 and an open topped enclosure 48 secured to the base plate 46. A stepper motor 50 is coupled to stepper motor gear unit 50' with the valve assembly 14 seated on motor shaft extender 52 which is secured to motor shaft 54. The rotor 16 is coupled to the shaft extender 52 secured to the motor shaft 54 for rotation with said shaft 54. The stator 18 is mounted to the housing 48 (the said housing being represented in broken outline in FIG. 1 as diagrammatically part of the stand 12, the housing per se being represented in FIG. 22). As shown in FIG. 1, the stator is above the rotor 16 and the surface 18" of stator 18 is superposed on, coaxial with and frictionally sealably engaged with, the surface 16' of said rotor 16. The rotor 16 as shown in FIG. 22 is shown below the stator, as will be described later.

Looking at FIGS. 1, 2, 4 and 22 (in FIG. 22 by primed reference characters), a closed inner end radial passageway 55' is formed in the rotor 16 opening to the circumferential surface 16''' of rotor 16 for receipt of pin 55. The stator 18,18A is provided with diametrically opposite openings 19,19', 19A and 19B to the outer circumferential surface 18",18A''' thereof for loosely receiving pins 66, 66' for supporting said stator 18. Passageways 67, 67' are formed through the upper portion of wall 48' at diametrically opposed locations, the pins 66, 66' being secured therein. The bores 19,19' are not visible from surface 18' and, in stator 18A, are bottom opening to surface 18A" of stator 18. An optical switch 68' is positioned on the top of wall 48' disposed at a predetermined location so that when aligned with pin 55, the rotor 16 is positioned at the zero or initiate position of said rotor. The arrangement 55 and 68 enables the initiate position for the operational cycle of the valve assembly 14 and particularly, the initiate position of the rotor 16 to be sensed. The base plate 46 includes an upstanding hollow hub formation 56 to accommodate the motor shaft 50 and shaft extender 52. An alignment bearing 51 (see FIG. 22) is seated within said hub formation 56'. The valve assembly 14 is secured in place by retainer nut 58' which is biased against the stator by compression spring 60' and retained in position properly centered coaxial with the rotor 16.

The balanced gimballed mounting arrangement 64, 64' by means of which the valve assembly 14 is mounted comprises the pins 66,66', bores 19,19' (notches 19A,19A') and the passageways 67,67'. The gimballed mounting 64, 64' further includes a coupling between the drive shaft extender 52 and the rotor 16, specifically at the hub or central passageway 82 thereof. A pin 57, 57' is secured through the shaft extender 52 so that it extends outward therefrom on diametrically opposite circumferential portions thereof. The rotor 16 is provided with slot portions 53,53' opening into the central opening 82 and located along a line 90 degrees angularly spaced from a line passing diametrically through central opening 84 and bores 19,19' (notches 19A, 19A') assembled. When the rotor 16 is mounted on the stator 18, the shaft extender 52 is slidably engaged through the central opening 82 with the pin 57,57' having its ends passing into the slot portions 53,53'. The fit is snug but leaves a slight freedom of movement for the rotor 16. Accordingly, the balanced gimballed mounting 64 provides a limited freedom of movement for each of the elements 16 and 18 of the valve assembly in that the stator is permitted bidirectionally to incline about the central axes of pins 66,66' while the rotor 16 is permitted the ability bidirectionally to incline about the central axis of pin 57,57'. In this way, the facing surface of the rotor will follow the inclining motion of the stator and vice versa. With this motion, the alignment of the respective passageways in the rotor and stator is maintained, notwithstanding the rotary movement of one of said valve elements relative to the other. This permits a body to incline freely in any direction or suspends it so that it will remain level when its support is tipped, say during the rotation of the rotor element 16. Thus the frictional engagement of the facing surfaces of the rotor 16 and stator 18 is maintained, assuring maintenance of the seal therebetween and prevention of leakage from the interior passageway junctions travelling along said surfaces to the exterior of the assembled valve assembly.

The resulting balanced gimballed mounting 64,64' assures the maintenance of the stator 18 and rotor 16 coaxially, with the respective surfaces 18" and 16' (in FIG. 1) and 18' and 16" (in FIG. 22) in frictional engagement and the respective through passageways formed in both rotor and stator in proper alignment overcoming the normal tendency of relatively rotating bodies to misalign. Thus the rotary motion of the rotor 16 during the rotation of the rotor throughout the various steps of the operational cycle of the valve assembly is not permitted to misalign the respective ports of the said passageways nor cause the surfaces 16' and 18" (FIG. 1) and 16" and 18' (FIG. 22) to disengage, thereby the seal therebetween is preserved. The misalignment that could occur may be described as vectorial misalignment which could occur when one of the assembled valve elements is driven relative to the other (stationary) valve element.

The term "balanced" is defined as a four point symmetrical gimballing of the two valve disc elements, the rotor and the stator in the embodiments described. The rotor is inclinable..limited freedom of movement ... ..bidirectionally about an axis taken diametrically through the central opening or hub thereof. The stator also is bidirectionally inclinable in the same manner except the axis is 90 degrees rotated from the axis of inclination of the rotor. The matched central passageways 82 and 84 of the rotor 16 and the stator 18 respectively being aligned, permit passage of the shaft portion 52 therethrough, with the pin 57,57', defining the driving coupling between the shaft extender portion 52 and the rotatable one of the valve elements, here, the rotor 16, so that rotation of the motor shaft 50 rotates the shaft extender portion 52 and the rotor 16.

As will be described hereinafter, the valve assembly 14 effects all the fluid handling functions for the system 10 and effectively replaces the now conventional, previously patented metering, transfer and delivery valve assemblies employed in prior particle study systems. The rotor 16 and stator 18 of valve assembly 14 each carry sets of associated segmenting passageways, each having precise interior volumes for the purpose of metering and isolating precise volume aliquots respectively of the blood sample to be tested, of diluent and of reagent, such as lysing reagent used to breakdown the red blood cells so as to permit the determination of hemoglobin and certain of the parameters, i.e. characteristics, of white blood cells. The rotor 16 and stator 18 each carry bridging loops completing each set of segmenting passageways. Also circulating passageways also are carried by each of said rotor 16 and stator 18 to establish select dedicated serial flow paths through the valve assembly 14 at stages in the operation of the valve assembly 14 for the purpose of leading the isolated aliquots of liquid sample, of diluent and of lyse reagent to the respective mixing vessels for passage through the Coulter sensing apertures where the signals are generated to provide the data for the parameter determinations to be performed. In the embodiment described herein, the rotor 16 is disposed below the stator 18 and is rotatable step by step serially. As will be explained later hereinafter, the positions of the rotor and stator can be reversed or interchanged, employing relatively apparent modifications. All but one of the metering functions are carried out utilizing the rotor 16 to effect segmentation, isolation and storage of the said liquid sample aliquots, the diluent aliquots and the lyse reagent aliquot (here only one lyse reagent aliquot is required), in respective steps. In the described embodiment, the stator 18 does carry one set of segmenting passageways employed to provide a liquid sample aliquot for use in determination of RBC (red blood cell) characteristic parameters. The movement of fluids within the valve assembly is effected primarily by application of vacuum to the directionally leading end of the body of fluid being moved with the trailing end of said body being followed by air due to the nearest port thereto being open to the atmosphere.

Figure 2:
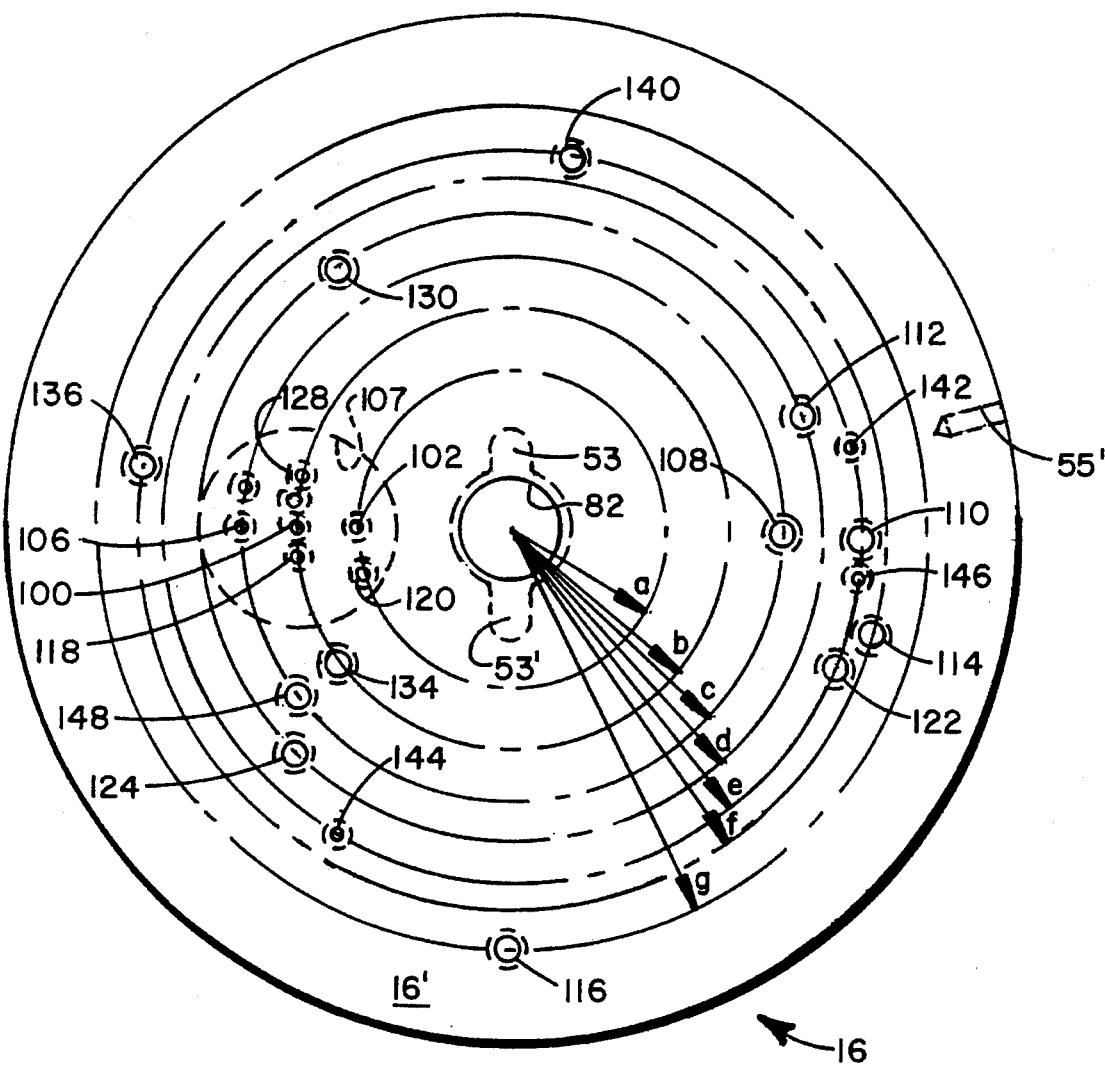
FIG. 2 is a plan view representing the rotor element of the valve assembly according to the invention.
Figure 3:
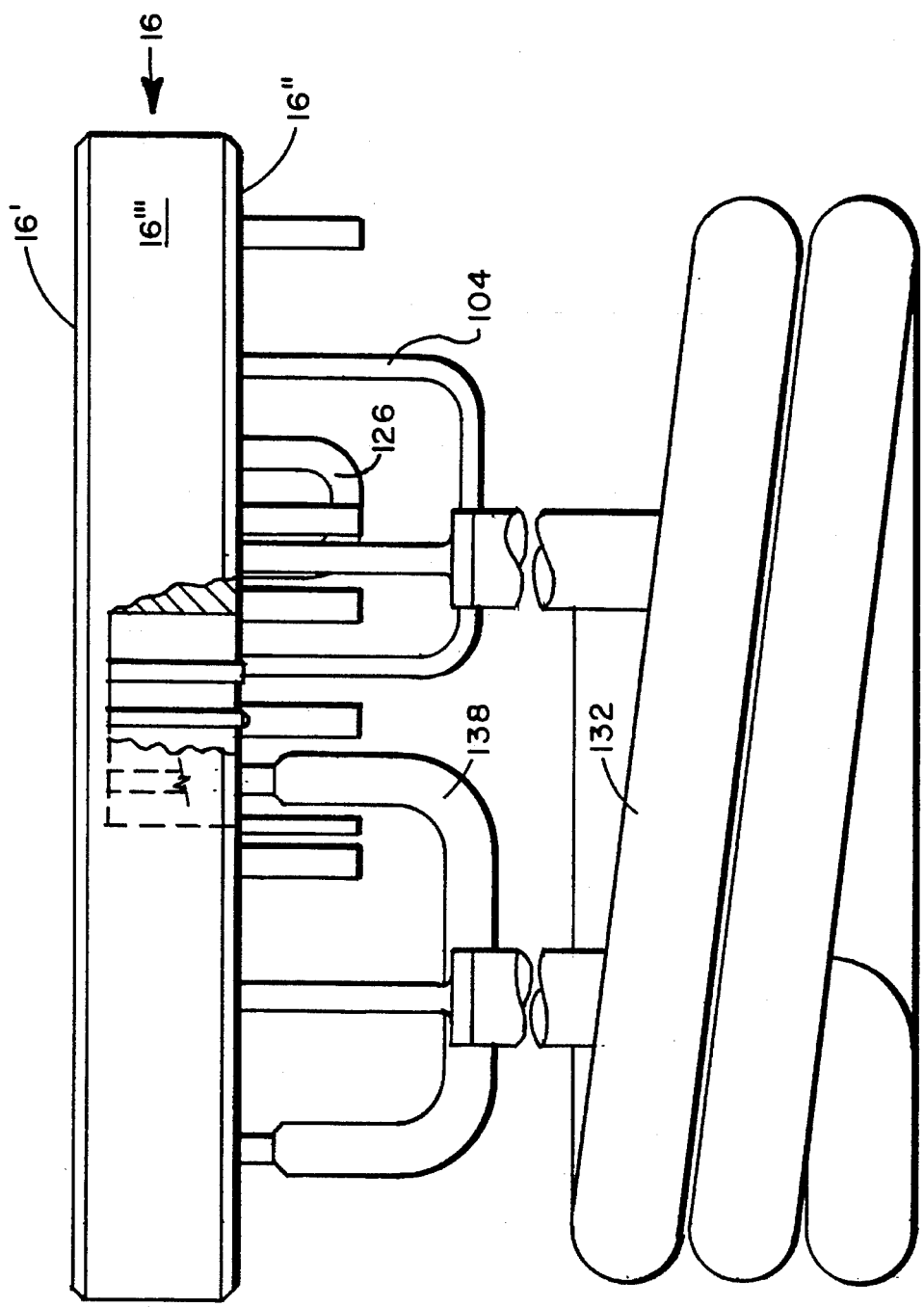
FIG. 3 is an enlarged diagrammatic fragmentary elevational view of the system illustrating the rotor portion of the valve assembly incorporated therein.
Figure 4:
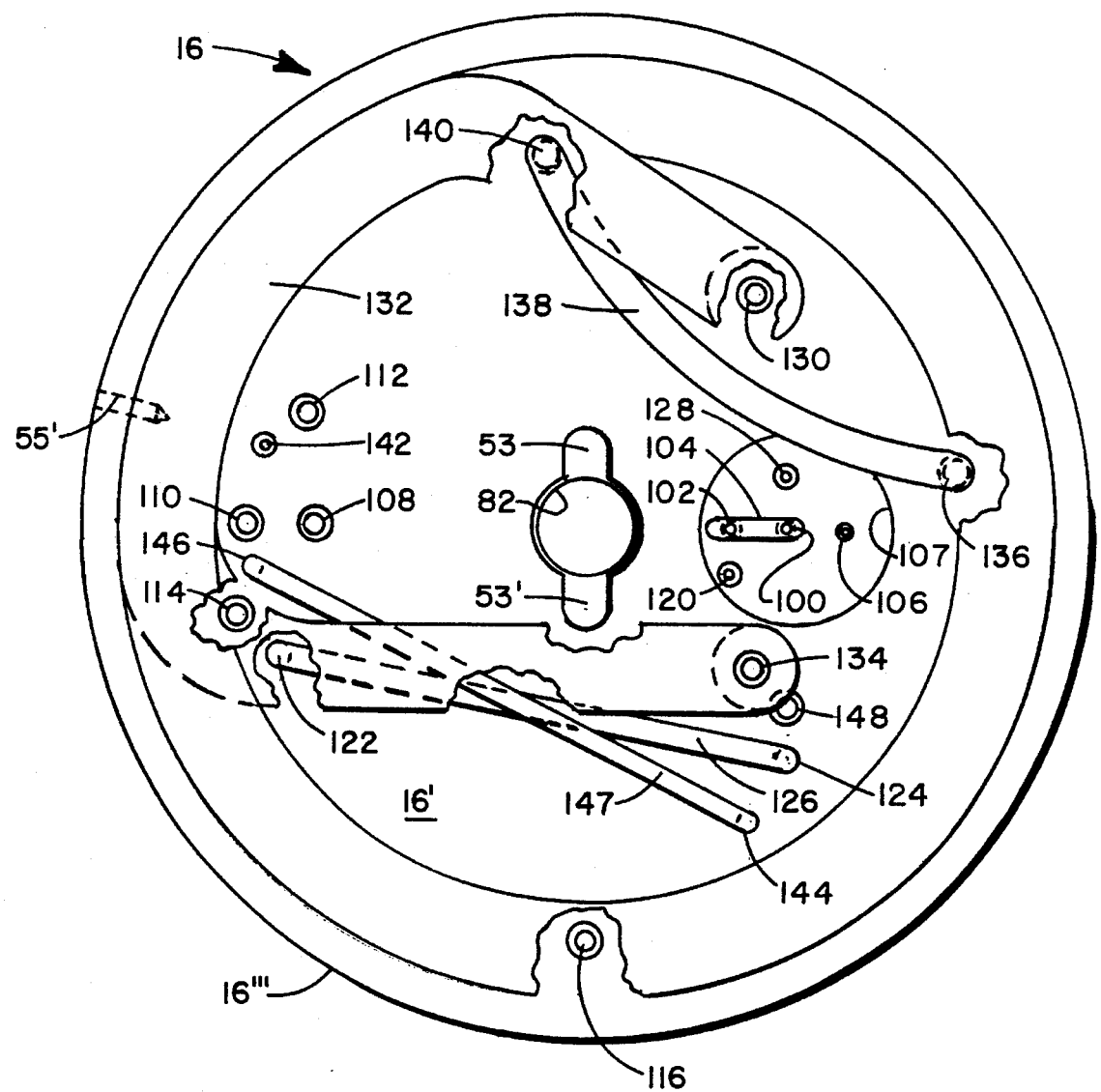
FIG. 4 is a plan view of the underside of the rotor element of the valve assembly according to the invention.
Figure 5:
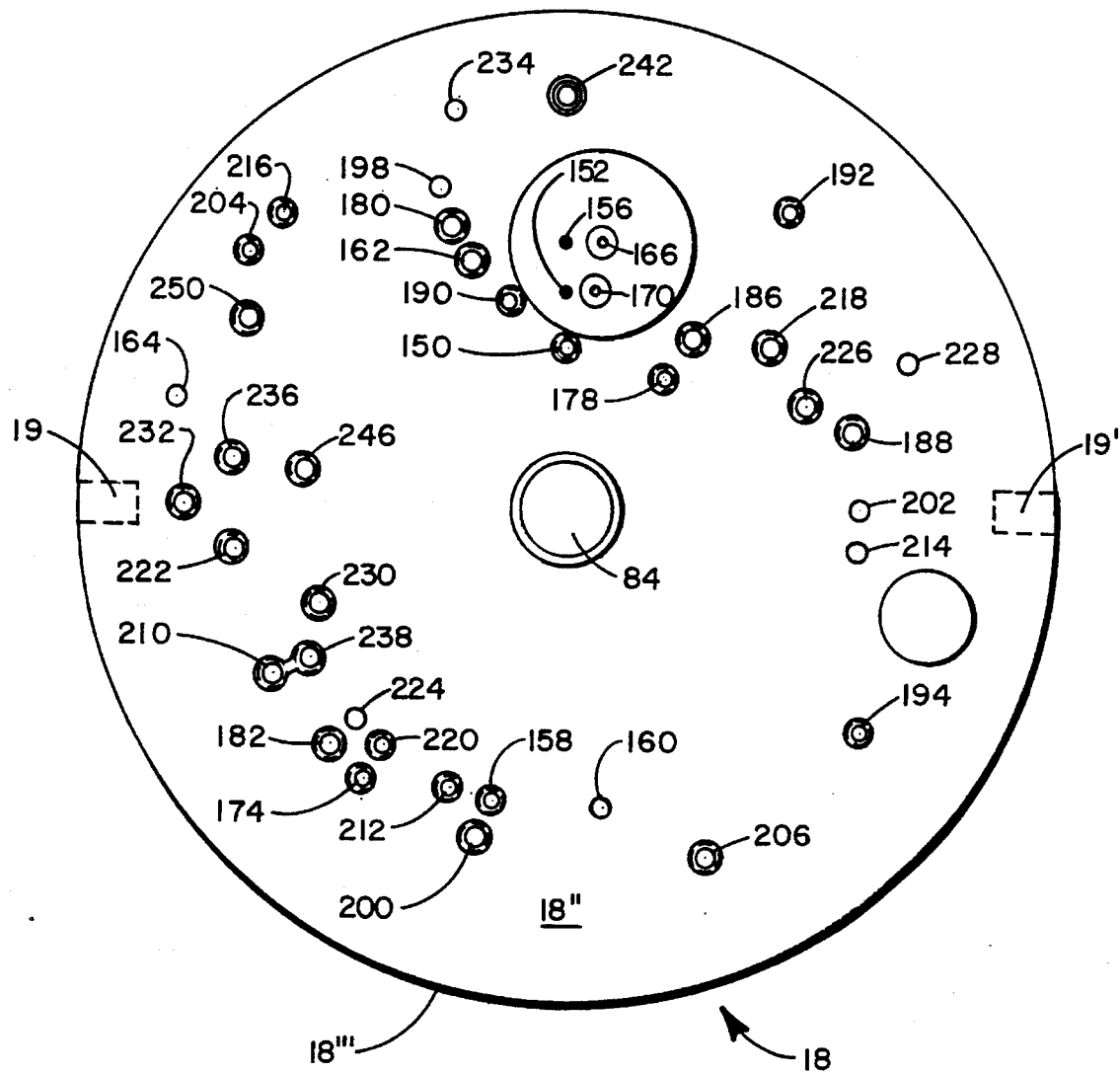
FIG. 5 is a plan view representing the stator element of the valve assembly according to the invention.

Referring to FIGS. 2 through 4, the rotor 16 is provided with axially parallel through passageways of preselected volume and/or diameter at selected radial distances from the axial center of axial passage 84 and along radial lines angularly spaced ones from the others. Likewise, the stator 18 also is provided with axially parallel through passageways of preselected volume and/or diameter at selected radial distances from the axial center of passage 82 and, also, locates selected groups of passageways along radial lines angularly spaced ones from the others. Each of these stator passageways have specific functions and cooperate with selected passageways carried by the rotor 16.

Now referring to FIG. 2, the rotor 16 carries blood segmenting passageways 100 and 102 linked by outwardly extending loop 104, each of precise interior volume and functioning to carry a desired aliquot of blood sample, the liquid sample to be considered in the herein description. An additional passageway 106 is included in this group and functions to be coupled by suitable conduit leading to the vacuum manifold 36' in turn coupled to a vacuum source (vacuum pump) 36.

Axially parallel through passageways 108, 110, 112, 114, 116 and 148 are circulating passageways which function to link the valve assembly 14 to the mixing vessels 42 and 44 by suitable conduit means intercoupling same. Through passageway 118 functions, along with through passageways 144 and 146 to introduce air from the atmosphere to the valve assembly 14 under the influence of vacuum applied during several of the operational steps of the system 10. Passageways 144 and 146 are linked by hollow loop 147. Through passageways 122 and 124 are coupled via loop 126 to define a diluent aliquot for delivery to the liquid sample aliquot disposed within passageways 100, 102 and loop 104 for delivery to the mixing vessel 42 so that determination of the WBC characteristics can be effected at the Coulter sensing aperture 42'. Through passageways 106, 128 and 142 are coupled to the vacuum source 36 via vacuum manifold 36'.

Through passageways 130 and 134 are carried by the rotor 16 and coupled by loop 132 and are capable of isolating a second diluent aliquot simultaneously with the isolation of the first diluent aliquot within the passageways 122, 124 and loop 126. This second diluent aliquot is employed during the delivery of the RBC sample aliquot while the first diluent aliquot is employed during the delivery of the WBC sample aliquot.

The rotor 16 passageways are located as follows with reference to their radial distances marked by distances a, b, c, d, e, f and g in FIG. 2 spaced from the center point of the axial passageway 84 and along radial lines taken from the center point of said rotor through the angular distance required for rotation of said rotor from its initial position following the steps of the operational cycle of the valve assembly 14, said position being 0 degrees. The radial distances represented are as follows, in inches: "a"=0.450 inches; "b"=0.600 inches; "c"=0.750 inches; "d"=0.850 inches; "e"=0.950 inches; "f"=1.050 inches; and, "g"=1.150 inches. Passageway 102 is distance "a" from the axial center and along a radial line at 0 degrees; passageway 102 is distance "b" from the axial center and along the radial line at 0 degrees; passageway 106 is distance "c" from the axial center and along the radial line at 0 degrees; passageway 108 is distance "c" from the axial center and along the radial line at 180 degrees; passageway 110 is distance "e" from the axial center and along the radial line at 180 degrees; and passageway 112 is distance "d" from the axial center and along the radial line at 157.5 degrees.

Passageway 114 is distance "f" from the axial center and along the radial line at 195 degrees; passageway 116 is distance "g" from the axial center and along a radial line 270 degrees; passageway 118 is distance "b" from the axial center and along a radial line 352.5 degrees; passageway 120 is distance "a" from the axial center and along a radial line 345 degrees; passageway 122 is distance "e" from the axial center and along a radial line 202.5 degrees; passageway 124 is a distance "d" from the axial center and along a radial line 315 degrees; passageway 128 is a distance "c" from the axial center and along a radial line 15 degrees; passageway 130 is a distance "d" from the axial center and along a radial line 52.5 degrees; passageway 134 is a distance "b" from the axial center and along a radial line 322.5 degrees; passageway 136 is a distance "f" from the axial enter and along a radial line 7.5 degrees; passageway 140 is a distance "g" from the axial center and along radial line 97.5 degrees; passageway 142 is a distance "e" from the axial center and along a radial line 165 degrees; passageway 144 is a distance "e" from the axial center and along a radial line 300 degrees; passageway 146 is a distance "e" from the axial center and along a radial line 187.5 degrees; and passageway 148 is a distance "c" from the axial center and along a radial line 327.5 degrees.

In FIGS. 3 and 4, the same reference characters designate the passageways and loops secured to the rotor 16. The functions of said passageways and loops will be evident from the description of the operational cycle that is set forth later in the description of the preferred embodiment of the invention referencing FIGS. 8 to 26.

Figure 6:
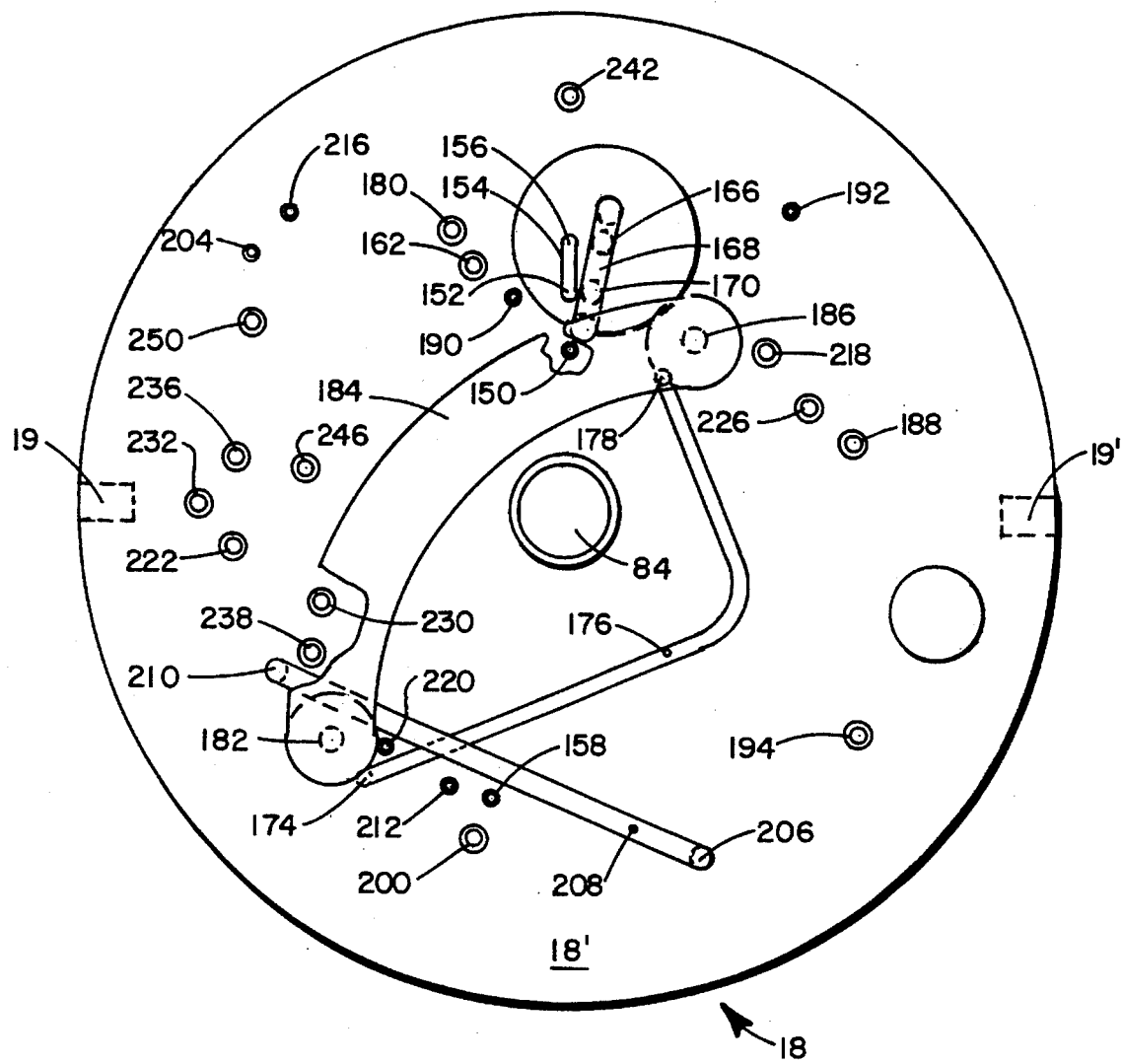
FIG. 6 is an enlarged diagrammatic fragmentary elevational view of the system illustrating the underside of the stator portion of the valve assembly according to the invention.
Figure 7:
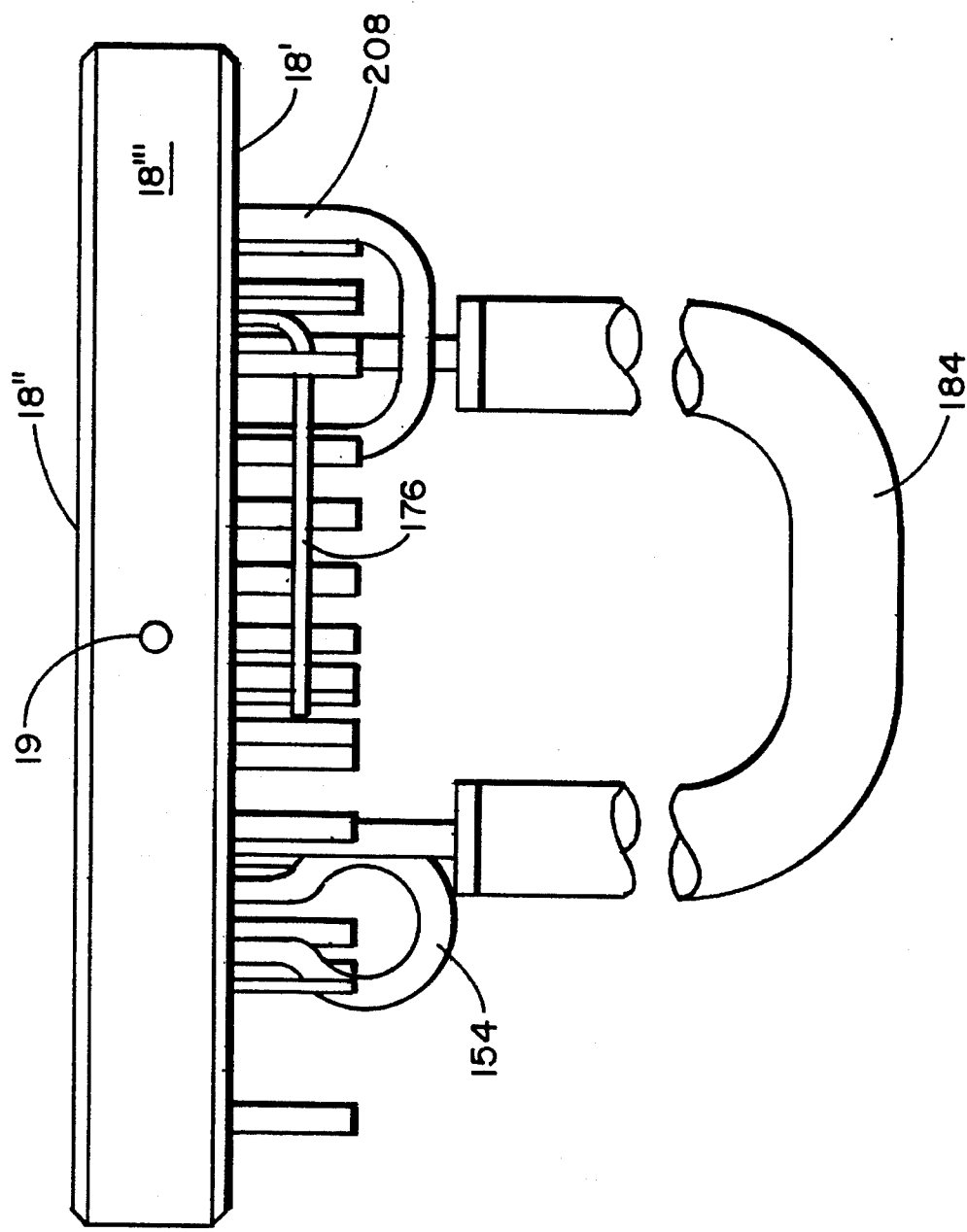
FIG. 7 is a top plan view of the stator element of the valve assembly according to the invention.
Figure 8:
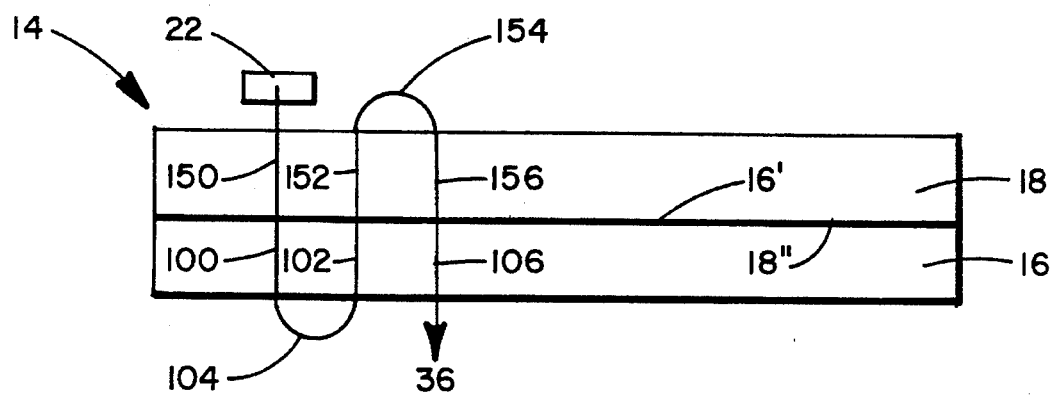
FIGS. 8 through 21 are diagrammatic representations illustrating the steps in the operational cycle of the system and the relationship of the ports of the rotor and stator of the valve assembly and the functional portions system according to the invention; and, FIG. 22 is an elevational view, portions in section, of a modified embodiment of the system according to the invention illustrating the rotor element superposed upon the stator element of the valve assembly.

Referring now to FIGS. 6 through 8, the stator 18 also is provided with a plurality of axially parallel through passageways. Passageway 150 is formed in stator 18 and functions as the entry for the blood sample into the valve assembly 14 from the sample source 22. Passageways 152 and 156, coupled by loop 154 is directly linked to passageway 102 so as to continue the first serial flow path defined within the valve assembly for accommodating the blood sample, establishing the continuous body of blood sample within the valve assembly 14 from which is isolated the sample aliquots respectively required for the WBC and the RBC determinations. Through axially parallel passageways 158, 162, 190, 194, 200, 212, 216, 218, 222, 226, 230 and 236 are carried by the stator 18 and function either to be coupled selectively to the vacuum source 36 via the vacuum manifold 36' or to be coupled selectively to certain through passageways formed in the rotor 16 or to the mixing vessels 42, 44 respectively during the operational cycle of said valve assembly 14 in accordance with the program of operation of the system 10.

Axially parallel through passageways 160, 198, 202, 214, 224, 228 and 234 open to the atmosphere to provide entry for air to be introduced to the valve assembly 14 under the influence of vacuum for moving the liquids within the valve assembly 14 at selected stages in the operation of the valve assembly 14. Passageways 166 and 170, coupled by loop 168, provide a communication path within the valve assembly 14 during one of the operations of the said valve assembly 14. Likewise, axially parallel through passageways 238, 242, 246 and 250 are intended to be coupled to a source 30 of cleaning reagent functioning during the steps of cleaning interior portions of the valve assembly 14 in the cycle of operation of said assembly 14, i.e. backwash. In order to accomplish backwash, some positive pressure can be utilized to force the cleaning reagent through the passageways 238, 242, 246 and 250 to drive said cleaning reagent to a contained reservoir itself under vacuum without permitting the said reagent to escape into the environment. Thus vacuum can be augmented by positive pressure without compromising the "closed system" character enabled by the invention.

Through passageways 182 and 186 linked by loop 184 function to aid in the transport of diluent along a second serial flow path during the loading of diluent into the valve assembly from the diluent source 24. Passageways 188, 130, 134 (linked by loop 132) and 190 define a third serial flow path during the loading of diluent into the valve assembly from the diluent source 26. The diluent aliquot for the determination of the WBC (white blood cell) characteristics is segmented from the second serial flow path while the diluent aliquot for the determination of the RBC characteristics is segmented from the third serial flow path. The flow path through stator passageways 182, 186 via loop 184 as well as the flow path through passageways 166 and 170 via loop 168 serve to direct sample and diluent respectively into the appropriate mixing vessels 42, 44. Passageway 192 serves as the entry for introduction of lyse reagent into the valve assembly 14 into and along a fifth serial flow path. Passageway 206 functions with circulating passageway 210 and loop 208 in the delivery of lyse reagent to the mixing vessel 42 so that the WBC determination can be effected as well as a hemoglobin determination can be obtained by optical means (not shown).

The passageways formed in the stator 18 are located with reference to the distances indicated in FIG. 6 representing distances from the axial center of the stator 18 and relative to the lines indicating the angular distances from the initial condition of the rotor 16 at 0 degrees. Passageway 150 is at distance "a" from the center and along a line 0 degrees; passageway 152 is at distance "b" from the axial center and along a line 0 degrees; passageway 156 is at distance "c" from the center and along a line 0 degrees; passageway 158 is at distance "d" and along a line 195.0 degrees; passageway 160 is at a distance "d" from the axial center and along a line 172.5 degrees; passageway 162 is at a distance "c" from the axial center and along a line 337.5 degrees; passageway 164 is at a distance "e" from the axial center and along a line 105 degrees; passageway 166 is at a distance "c" and along a line 7.5 degrees; passageway 170 is at a distance "b" and along a line 7.5 degrees; passageway 174 is at a distance "e" and along a line 37.5 degrees; passageway 178 is at a distance "a" from the axial center and along a line 37.5 degrees; passageway 180 is at a distance "d" from the axial center and along a line 157.5 degrees; passageway 182 is at a distance "e" from the axial center and along a line 45 degrees; passageway 186 is at a distance "d" from the axial center and along a line 37.5 degrees; passageway 188 is at a distance "d" from the axial center and along a line 75 degrees; passageway 192 is at a distance "f" from the axial center and along a line 37.5 degrees; passageway 194 is at a distance "f" from the axial center and along a line 127.5 degrees; passageway 198 is at a distance "e" from the axial center and along a line 157.5 degrees; passageway 200 is at a distance "e" from the axial center and along a line 195 degrees; passageway 202 is at a distance "d" from the axial center and along a line 90 degrees; passageway 204 is at a distance "f" from the axial center and along a line 127.5 degrees; passageway 206 is at distance "f" from the axial center and along a line 157.5 degrees; passageway 210 is at a distance "e" from the axial center and along a line 240 degrees; passageway 212 is at a distance "d" from the axial center and along a line 202.5 degrees; passageway 214 is at a distance "d" from the axial center and along a line 97.5 degrees; passageway 216 is at a distance "g" from the axial center and along a line 315 degrees; passageway 218 is at a distance "c" from the axial center and along a line 52.5 degrees; passageway 220 is at a distance "d" from the axial center and along a line 37.5 degrees; passageway 222 is at a distance "e" from the center and along a line 82.5 degrees; passageway 224 is at a distance "d" from the axial center and along a line 45 degrees; passageway 226 is at a distance "c" from the axial center and along a line 67.5 degrees; passageway 228 is at a distance "f" from the axial center and along a line 67.5 degrees; passageway 230 is at a distance "c" from the axial center and along a line 67.5 degrees; passageway 232 is at a distance "f" from the axial center and along a line 90 degrees; passageway 236 is at a distance "e" from the axial center and along a line 97.5 degrees; passageway 238 is at a distance "d" from the axial center and along a line 240 degrees; passageway 242 is at a distance "g" from the axial center and along a line 0 degrees; passageway 244 is at a distance "c" from the axial center and along a line 97.5 degrees; and, passageway 246 is at a distance "f" from the axial center and along a line 300 degrees.

Referring now to FIGS. 8 through 21, in these FIGURES, passageway entries indicated by reference characters 38A (and the inwardly directed arrows) generally are open to the atmosphere. Passageway entries indicated by reference character 38B (and the inwardly directed arrows) can be coupled optionally to a source of pressurized inert gas (air) such as an air pump 38. In the course of this description, vacuum is drawn on the passageway defining the leading end of the particular body of liquid in the particular flow path, if the trailing end of that particular flow path is open to the atmosphere, air is drawn against the said trailing end to exert a force thereagainst. It is feasible, under some circumstances, to introduce pressurized fluid such as pressurized air or pressurized inert gas, such as from air pump 38, to contribute some force against the said trailing end of the liquid body, thereby aiding in the flow of liquid forming said body. The use of pressurized fluid either via the air pump 38 or simply by leaving the air entry open to the atmosphere when vacuum is applied to the entry end of the fluid body in the flow path concerned.

It should be understood that although the application of vacuum is employed to move the liquid bodies within the valve assembly, the use of pressure to move such bodies or to supplement the vacuum, is contemplated.

In FIG. 8 the initial step of the operational cycle of the valve assembly 14 is illustrated with the rotor 16 stationed at 0 degrees, the rotor passageway 100 being aligned with the stator passageway 150; the rotor passageway 102 aligned with stator passageway 152 and the stator passageway 156 aligned with the rotor passageway 106. The remaining passageways are blocked by the facing surfaces of the rotor and stator elements. Rotor passageways 100 and 102 are linked by the hollow loop 104 and stator passageways 152 and 156 are linked by the hollow loop 154, thereby defining a first serial flow path through the valve assembly 14, the blood sample flow path, from which the blood sample aliquots are segmented and isolated. The blood sample flow path can be followed from the sample source 22 to passageway 150 to passageway 100, through passageway 104 to passageway 102 through passageway 152 to passageway 154 to passageway 156 to passageway 106 to the vacuum source 36. At the initial stage of the operational cycle of valve assembly 14, all passageways have been cleared and contain air. The mixing vessels 42 and 44 contain diluent. Rotor passageway 106 is coupled to said vacuum source 36 via vacuum manifold 36'. The loading step of the valve assembly is initiated by drawing vacuum on passageway 106, causing liquid blood sample to be drawn from the blood sample source 22 and to enter the valve assembly via stator passageway 150 and through the first flow path to define a continuous serial liquid sample body.

Figure 9:
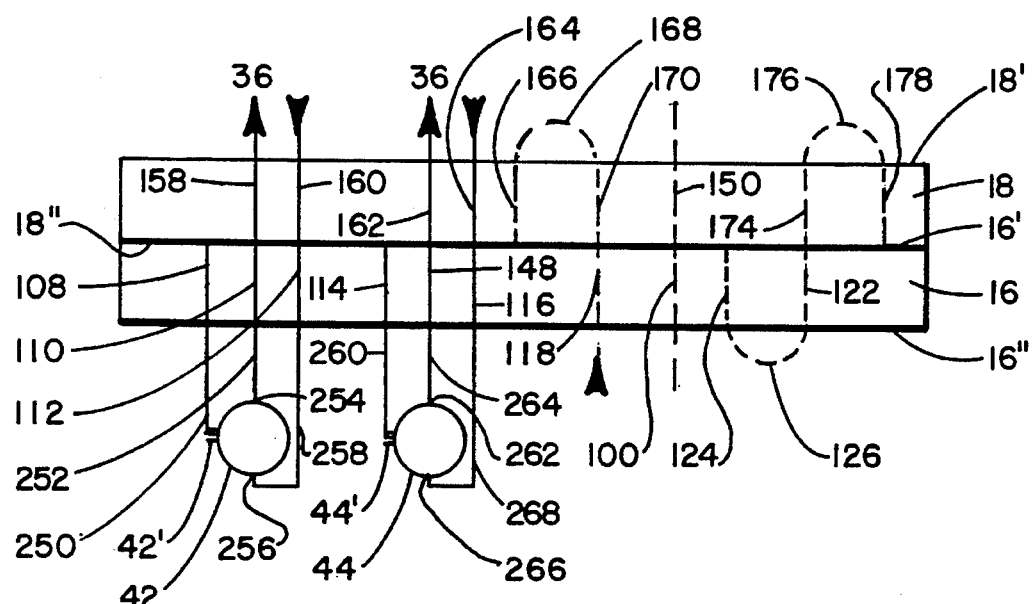

The rotor 16 next is translated rotatably, here 15 degrees, to position the valve assembly 14 at its second operational stage, represented in FIG. 9 at which step the mixing vessels 42 and 44 are cleared of diluent and replaced with air. The rotor passageway 108 is positioned to communicate, via conduit 246 to the sensing aperture 42' leading to the mixing vessel 42 but passage through said passageway 108 is blocked within the valve assembly 14 by the surface 18". Rotor passageway 110 is coupled via conduit 252 to the inlet 254 of vessel 42. Rotor passageway 112 is coupled to the outlet 256 of mixing vessel 42 by conduit 258. Interior of the valve assembly 14, stator passageway 158 is aligned with rotor passageway 110 and stator passageway 160 is aligned with rotor passageway 112. Rotor passageway 114 is coupled to the sensing aperture 44' via conduit 260 leading to the mixing vessel 44 but passage through said passageway 114 is blocked within the valve assembly 14 by the surface 18" of stator 18 on the interior of said valve assembly 14. Rotor passageway 148 is coupled to the inlet 262 of the mixing vessel 44 by conduit 264 and, interior of the valve assembly 14, is aligned with stator passageway 162. Stator passageway 162 is coupled with the vacuum source 34 via vacuum manifold 36. Rotor passageway 116 is coupled to the outlet 266 of mixing vessel 44 via conduit 268. Stator passageways 160 and 164 are open to the atmosphere to permit entry of air therein to when vacuum is drawn on stator passageways 158 and 162, thereby forcing air into the mixing vessels 42 and 44, clearing said vessels, During this second stage in the operation of the valve assembly 14, the rotor passageway 124 and the stator passageways 166, 178 are blocked by surface 16' of rotor 16. Rotor passageway 118 is aligned with stator passageway 170 and rotor passageway 102 is aligned with stator passageway 174. When the mixing vessels 42 and 44 have been cleared, the second stage of the operation of valve assembly 14 is completed.

It should be noted that when the rotor 16 is translated from the first stage to the second stage, two sample aliquots are isolated, i.e. segmented from the first serial flow path, and these aliquots are stored within the rotor passageways 100, 102 and loop 104 (the aliquot to be used in the WBC determination) and within the stator passageways 152,156 and loop 154 (the aliquot to be used in the RBC determination) for later retrieval.

Figure 10:
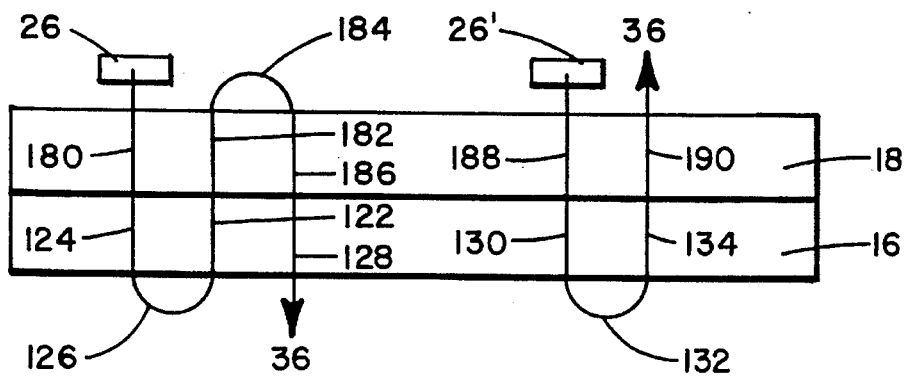

The programmable control 20 now causes the stepper motor 50 to translate the rotor 16 an angular distance of 7.5 degrees to a position 22.5 degrees from the initial or start position of said rotor 16 to reach the third stage of the operational cycle as represented in FIG. 10. At said third stage, rotor passageway 124 is aligned with stator passageway 180 and rotor passageway 122 is aligned with stator passageway 182. Rotor passageway 128 is aligned with stator passageway 186 defining a second serial flow path through the valve assembly 14, said second serial flow path being independent from the first serial flow path and dedicated to passage of diluent. Also, at this third stage, stator passageway 188 is aligned with rotor passageway 130 and rotor passageway is aligned with stator passageway 190 to define a third serial flow path through the valve assembly, said third serial flow path being independent from the first and second serial flow paths and also dedicated to passage of diluent. The second serial flow path for loading diluent receives diluent from the diluent source 26 to passageway 180 to and through passageway 124 to and through loop 126 to and through passageway 122 to and through passageway 182 to and through loop 184 to and through passageway 186 to and through passageway 128 for coupling to the vacuum source 36 via vacuum manifold 36'. The third serial flow path for loading diluent receives diluent from diluent source 26' into passageway 188 to and through passageway 130 to and through loop 132 to and through passageway 134 to and through passageway 190 for coupling to the vacuum source 36 via vacuum manifold 36'. With stator passageway 180 and stator passageway 188 coupled to diluent sources 26 and 26' respectively, and the passageways 128 and 190 coupled to the vacuum source 36 via the vacuum manifold 36' vacuum is drawn, causing diluent to be introduced to the said second and third serial flow paths to fill same, completing the third stage of the operational cycle of the valve assembly 14.

The rotor 16 next is translated an additional angular distance of 7.5 degrees to a position angularly 30 degrees from the initial condition of the rotor reaching the fourth stage of the operational cycle. Rotation of the rotor 16 effects segmentation of the second and third serial flow paths respectively and simultaneously, with the resulting diluent aliquots isolated and stored for later retrieval within the group passageways 134, 130 and loop 132, group passageways 124, 122 and loop 126 and group passageways 182, 186 and loop 184 respectively.

Figure 11:
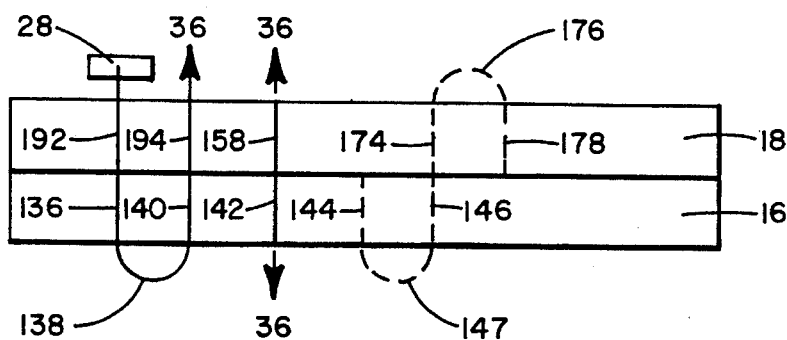

At the fourth stage in the operational cycle of the valve assembly 14, represented in FIG. 11, lyse reagent is loaded into the valve assembly 14. Rotor passageways 136 and 140 are aligned respectively with stator passageways 192 and 194. Stator passageway 192 functions to introduce the lyse reagent into the valve assembly 14 along a fourth independent dedicated flow path therethrough. Stator passageway 194 is coupled to the vacuum source 36 via vacuum manifold 36'. Rotor passageways 142 and 144 are blocked by the surface 18" of stator 18 while the stator passageway 178 is blocked by the surface 16' of rotor 16. Rotor passageway 142 and stator passageway 158 are each coupled to the vacuum source 36 via vacuum manifold 36'. Rotor passageway 146 and stator passageway 174 are aligned. When vacuum is drawn on passageway 194, lyse reagent is drawn into the valve assembly 14 from the source 28 of lyse reagent along said fourth serial flow path defined through passageways 192 and 136, loop 138, passageways 140 and 194 to define a serial body of lyse reagent therealong. Vacuum simultaneously also is drawn on passageways 142 and 158 with no liquid movement effect since vacuum is pulling in opposite directions out of passageways 142 and 158. A fifth serial flow path which is defined by passageways 144, 146, loop 147, passageway 174, loop 176 and passageway 178 is not utilized since it is blocked at opposite ends thereof by the engaged surfaces 16' and 18" of the rotor and stator elements, 16 and 18 respectively. Attention is directed to the fact that the said fifth serial flow path still is filled with air.

Figure 12:
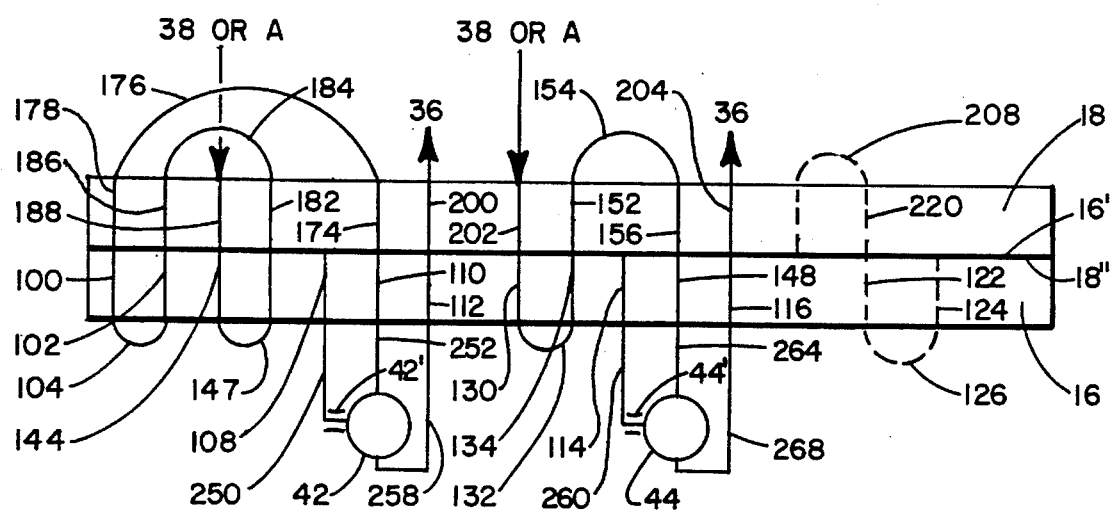

The fifth stage in the operational cycle of the valve assembly 14 is represented in FIG. 12 and initiated by rotation of the rotor 16 an additional step of 7.5 degrees, disposing the same at a position angularly 37.5 degrees from its initial condition, By such rotation, the fourth serial flow path dedicated to and containing lyse reagent, is segmented to isolate the lyse reagent aliquot disposed in rotor passageway 136, loop 138 and rotor passageway 140, wherein it is stored for later retrieval. When the rotor 16 has reached the fifth stage in the operational cycle of valve assembly 14, the first step of a two-step delivery process is initiated for delivering the stored sample and diluent aliquot pairs to the mixing vessels 42 and 44 respectively.

Figure 13:
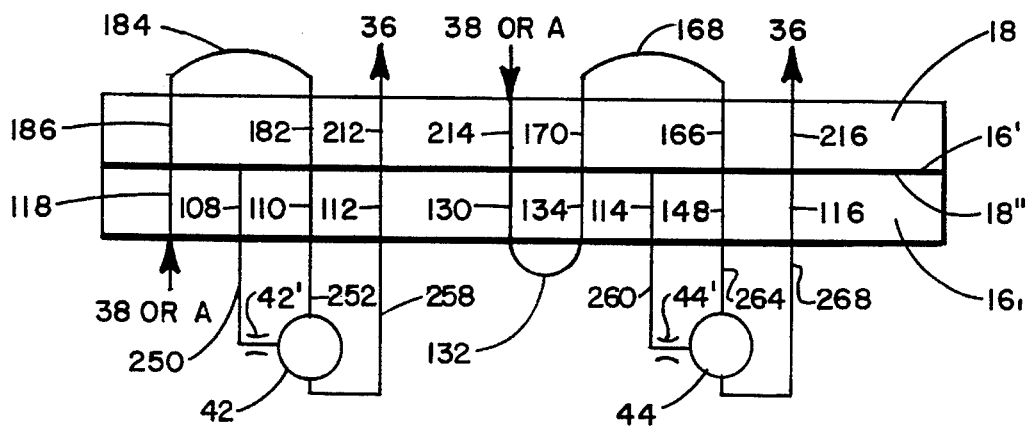

At the fifth stage, rotor passageways 100 and 102 are aligned with stator passageways 178 and 186 respectively. Rotor passageways 144 and 146 are aligned with stator passageways 198 and 182 respectively. Rotor passageway 108 is blocked by surface 18". Rotor passageway 110 is aligned with stator passageway 174 and rotor passageway 112 is aligned with stator passageway 200. Also, at the fifth stage, rotor passageways 130 and 134 are aligned with stator passageways 202 and 152 respectively and rotor passageway 114 is blocked by surface 18" of stator 18. Rotor passageways 148 and 116 are aligned with stator passageways 156 and 204 respectively. Stator passageway 206 is blocked by surface 16' of rotor 16 and stator passageway 210 is aligned with rotor passageway 122, rotor passageway 124 being blocked by the surface 18" of stator 18. Vacuum is drawn on stator passageways 200 and 204 simultaneously causing air to be introduced via stator passageways 198 and 202 respectively forcing the delivery of the content of the passageways 144, 146, loop 147, 182, loop 184, passageway 186; rotor passageway 102, loop 104, passageway 100; passageway 178, loop 176, stator passageway 174; and rotor passageway 110 to the mixing vessel 42. Simultaneously, the content of stator passageway 202; rotor passageway 130, loop 132, rotor passageway 134; stator passageway 152, loop 154, stator passageway 156; and rotor passageway 148 is introduced into the mixing vessel 44. Thus the isolated and stored sample aliquots and diluent aliquots are delivered, with some additional predetermined amount of diluent, to the respective mixing vessels 42 and 44 respectively, Now the programmable control 20 operates to rotate the rotor 16 a further 7.5 degrees to reach a position 45.0 degrees from the initial condition of rotor 16 and is now at the sixth stage in the operational cycle of valve assembly 14. The relative disposition of the respective passageways at the sixth stage is represented in FIG. 13. At the sixth stage, the introduction of the remaining diluent aliquots is completed, vacuum being continued thereafter to form and introduce air, as descrete and predetermined size air bubbles, into the mixing vessels of the respective components therein. Reaching the sixth stage, rotor passageway 118 and stator passageway 186 are aligned; stator passageway 182 and rotor passageway 110 also are aligned; stator passageway 182 and rotor passageway also being aligned. Rotor passageway 112 is aligned with stator passageway 212. Also at the sixth stage, stator passageway 214 is aligned with rotor passageway 130 and rotor passageway 130 and rotor passageway 134 is aligned with stator passageway 170. Stator passageway 166 is aligned with rotor passageway 148. Rotor passageway 116 is aligned with stator passageway 216. When vacuum is drawn simultaneously on stator passageways 212 and 216 simultaneously, the addition of the respective diluent aliquots is completed, along with the introduction of air, preferably in the form of intermittent air bubbles, to the respective mixing vessels 42 and 44.

Figure 14:
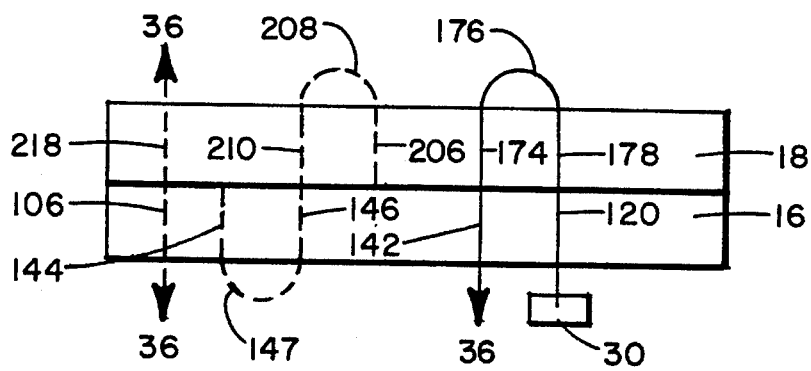

The rotor 16 then is translated an additional 7.5 degrees to dispose the valve assembly 14 at the seventh stage in its operational cycle where the rotor 16 is disposed 52.5 degrees from its initial orientation at the beginning of the operational cycle, the relationship of the respective passageways being illustrated in FIG. 14. The seventh stage in the operational cycle of the valve assembly, and hence, the system 10, involves the introduction of cleaner reagent to the transmission passageways within the valve assembly 14, particularly stator passageways 174 and 178. At this seventh stage, rotor passageway 142 is aligned with the stator passageway 174 and rotor passageway 120 is aligned with stator passageway 178. Rotor passageway 120 is coupled to a source 30 of cleaner reagent. Rotor passageway 106 is aligned with the stator passageway 218. The flow path defined along stator passageway 206, loop 208, stator passageway 210, rotor passageway 146 and rotor passageway 144 is unused since same is blocked at both ends by the rotor surfaces 16' and 18". Vacuum is drawn simultaneously on passageways 142, 106 and 218, drawing cleaner reagent from the source 30 of cleaner reagent into passageway 142 and having no effect on other fluid movement. As mentioned, it may be feasible to apply positive pressure such as from air pump 38, to move the cleaner reagent from the passageways 142, 106, 218 supplementing the vacuum drawn. The waste receptale W can be under slight vacuum. During the disposition of the valve assembly 14 at its seventh stage in the operational cycle, the volumes within the mixing vessels 42, 44 are not moved, being retained therein so that the mixing process therewithin is allowed to continue.

Figure 15:
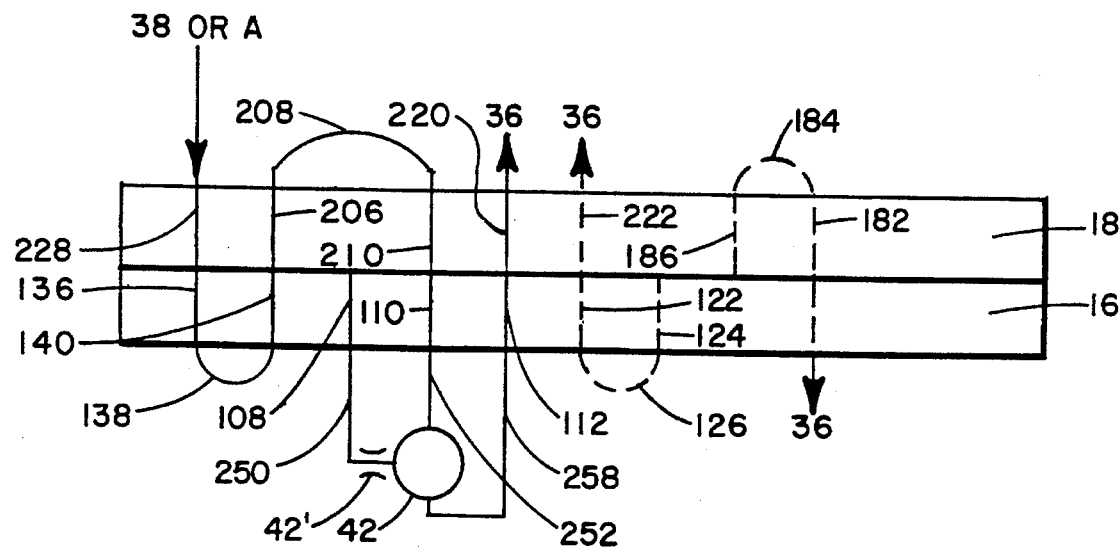

The programmable control 20 next operates the rotor 16 to cause translation thereof to reach the eighth stage of the operational cycle by rotating the rotor 16 another 7.5 degrees, bring the rotor 16 to a condition 60.0 degrees from its initial condition. When the valve assembly 14 is reaches the eighth stage, as represented in FIG. 15, the lyse reagent aliquot, which had been isolated and stored in rotor passageways 136, 140 and loop 138, is delivered to the mixing vessel 42. At the eighth stage, the rotor passageway 136 is aligned with passageway 228. Stator passageway 206 is aligned with rotor passageway 140 and is coupled to stator passageway 210 by loop 208. Rotor passageway 110 is aligned with stator passageway 220. Rotor passageway 108 is blocked by the surface 18" of stator 18. Rotor passageway 112 and stator passageway 222 are aligned. Rotor passageway 124 and stator passageway 186 are blocked by the facing surfaces 18" and 16' of the stator and rotor respectively. Rotor passageway 142 and stator passageway 182 are blocked by the facing surfaces 18" and 16' of the stator and rotor respectively. Rotor passageway 142 and 182 are aligned. When vacuum is drawn on passageways 222 and 142, the contents remaining in the flow path defined by passageways 124, 122, loop 126, passageway 228 and the flow path defined by passageway 186, loop 184 and passageway 184 are directed to waste W intermediate the vacuum source 36. Vacuum is drawn on passageway 220 causing air to be introduced at passageway 228, the vacuum driving the lyse aliquot in passageways. 136, 140 and loop 138 into the mixing vessel 42. The vacuum is continued for a predetermined length of time so that air is introduced into said vessel 42, preferably intermittently as air bubbles, for mixing the resulting content of said vessel 42.

Figure 16:
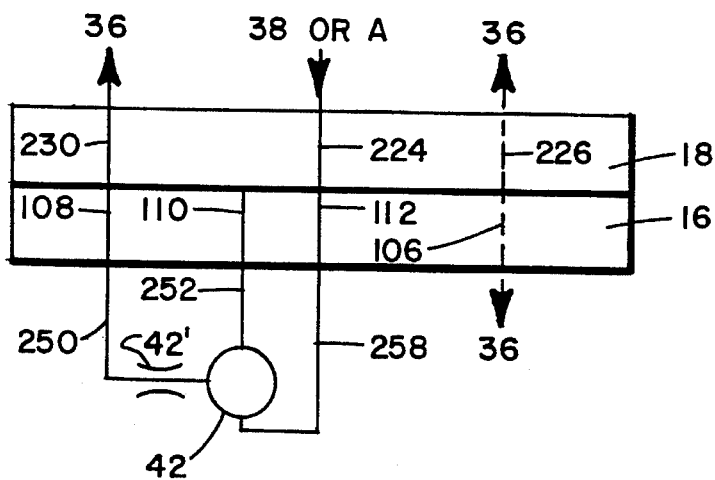

After a predetermined elapse of time sufficient to permit the lyse reagent to stromatolyse the red blood cells in the mixture within the vessel 42, the rotor 16 is translated rotationally another 7.5 degrees to reach the ninth stage in the operational cycle, represented in FIG. 16. At the ninth stage, rotor passageways 108 and 112 are aligned with stator passageways 230 and 224 respectively, with rotor passageway 106 and stator passageway 226 being aligned. Vacuum is drawn on passageway 230 causing the lysed suspension within the mixing vessel 42 to pass through the Coulter electronic sensing aperture 42' for the determination of the WBC characteristics, the generated electrical signals being transmitted to the analyzing apparatus of the system.

Figure 17:
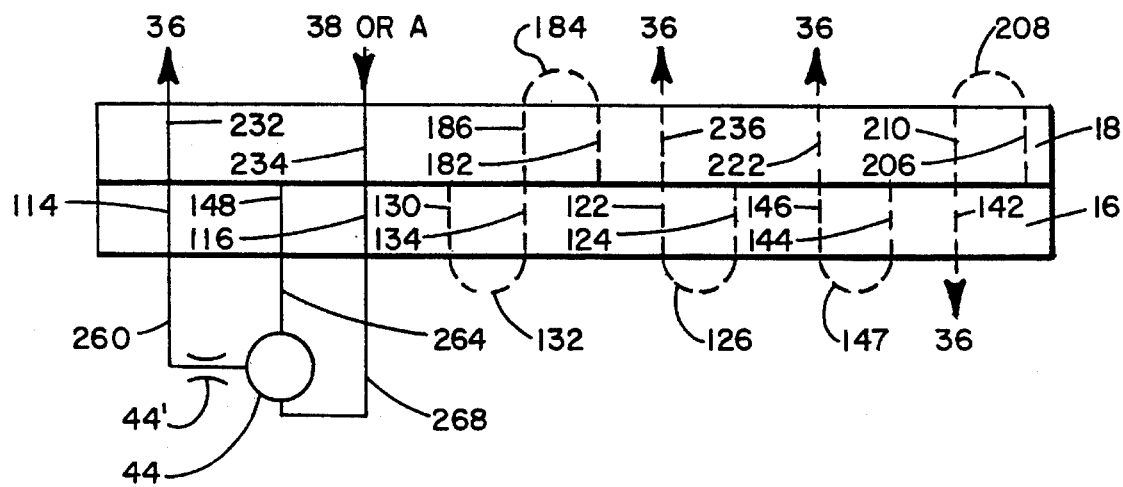

Referring to FIG. 17, after the completion of the sensing of the suspension from the mixing vessel 42 has been completed, the programmable control means 20 causes the rotor 16 to be translated a further 7.5 degrees to reach a position 75 degrees angularly from the initial condition of the rotor 16, assuming the tenth stage in the operational cycle of the valve assembly 14. The stator passageway 232 and rotor passageway 114 are aligned. The rotor passageway 148 is blocked by the surface 18" of stator 18 while passageway 116 is aligned with stator passageway 234. The flow path along passageway 130, loop 132, passageway 134, passageway 186 and loop 184 are blocked at their interior ends by the facing surfaces 18" and 16' of said elements 18 and 16. The flow paths defined respectively by passageway 124, loop 126, passageway 122 and passageway 236, and by passageway 144, loop 147, passageway 146 and passageway 222 are coupled to the vacuum source 36. Passageway 206, loop 208, passageway 210 and passageway 142 define a flow path which is coupled to the vacuum source 36 via the vacuum manifold 36'. Vacuum is drawn on passageway 232 causing air to enter stator passageway 234 and, pass through rotor passageway 116, travel along conduit 268 to enter the mixing vessel 44. Thus air entering the mixing vessel 44 and the vacuum drawn on passageway 232 causes the suspension from vessel 44 to be passed through the Coulter electronic sensing aperture 44'. Signals generated by the passing of the suspended particles through said sensing aperture 44' are transmitted to the analyzing apparatus of the system 10 for determination of the RBC characteristics of the blood sample. Simultaneously with the drawing of vacuum on passageway 232, vacuum is drawn on passageways 236, 222 and 142, driving the contents of passageways 124, 122 and loop 126; passageways 144, 146 and loop 147; and passageways 206, 210 and loop 208 to waste W.

Figure 18:
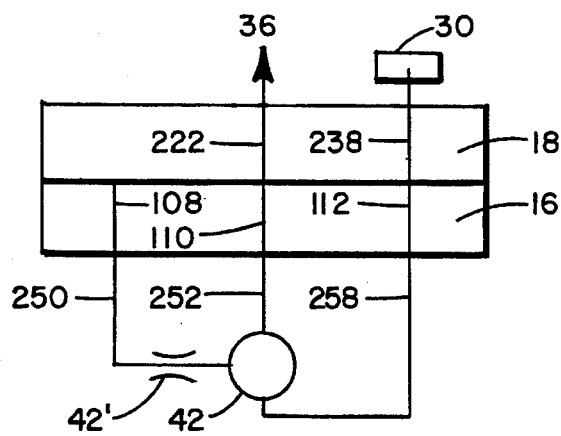
Figure 19:
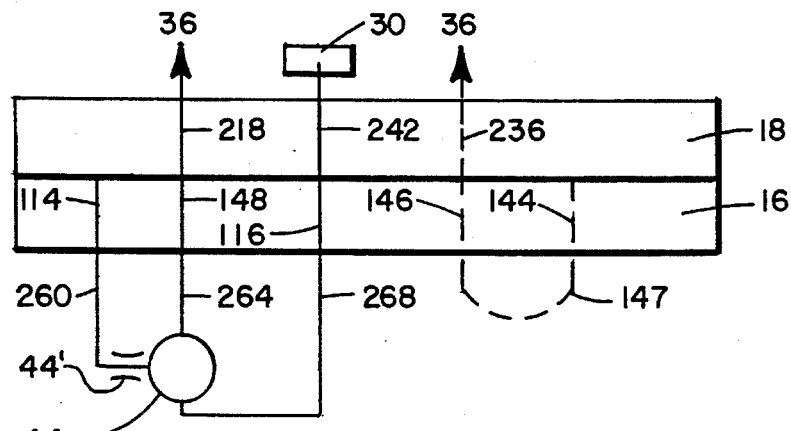

The next two stages of operation of the valve assembly 14 represented in FIGS. 18 and 19 are concerned with the cleaning of the mixing vessels 42 and 44 and associated passageways in the rotor and stator for readying the valve assembly in condition for the next sample to be tested. After the tenth stage has been completed, the rotor 16 is caused to be translated a further 7.5 degrees to reach a position 82.5 degrees from the initial position of rotor 16 whereby to assume the eleventh stage of the operational cycle of the valve assembly 14 as represented in FIG. 18. At this stage, passageway 108 is blocked at its inner end by the surface 18" of stator 18. Rotor passageway 110 is aligned with stator passageway 222. Passageway 238 is coupled to the source 30 cleaner reagent. Vacuum is drawn on stator passageway 222, causing cleaner liquid to be introduced to stator passageway 238 and, via passageway 112, through conduit 258 to the mixing vessel 42 to and through passageway 110 and passageway 222 to waste.

When the cleaning of mixing vessel 42 has been completed, the rotor 16 is translated an additional 7.5 degrees to a position 90.0 degrees from its initial position, represented in FIG. 19 whereat the mixing vessel 44 is cleaned. In this 12th stage of the operational cycle, rotor passageway 114 is blocked by surface 16' interior of the valve assembly 14. Passageway 242 is coupled to the source 30 of cleaner reagent. Passageways 144 and 146 are linked to stator passageway 244. Vacuum is drawn on both passageways 218 and 236, causing cleaner reagent to be drawn through passageway 242, to and through passageway 116, through conduit 268 to enter mixing vessel 44 and thence, via rotor passageway 148 and stator passageway 218 to waste. The content of rotor passageway 144 and 146 are drawn exterior of the valve assembly 14 via stator passageway 236 and directed to waste.

Figure 20:
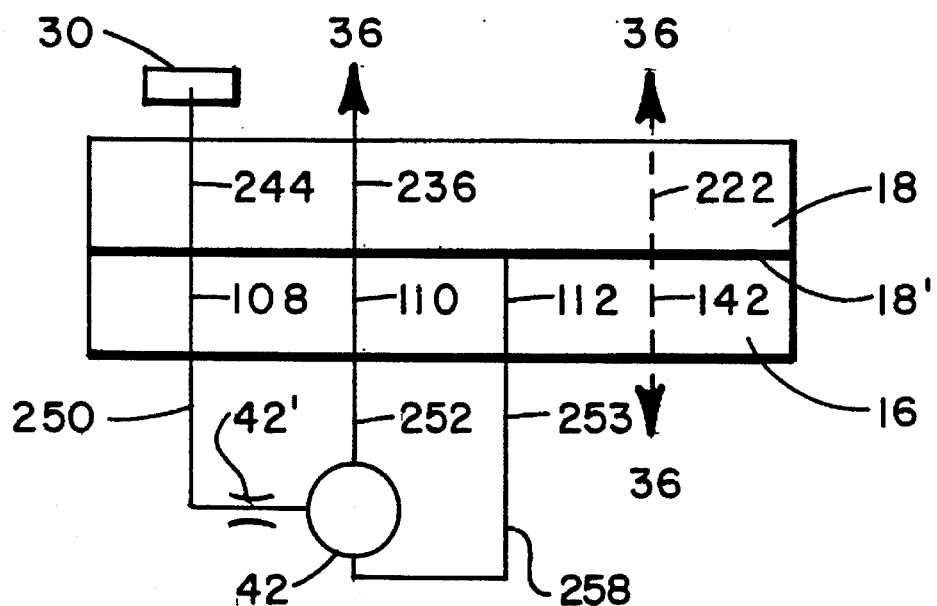
Figure 21:
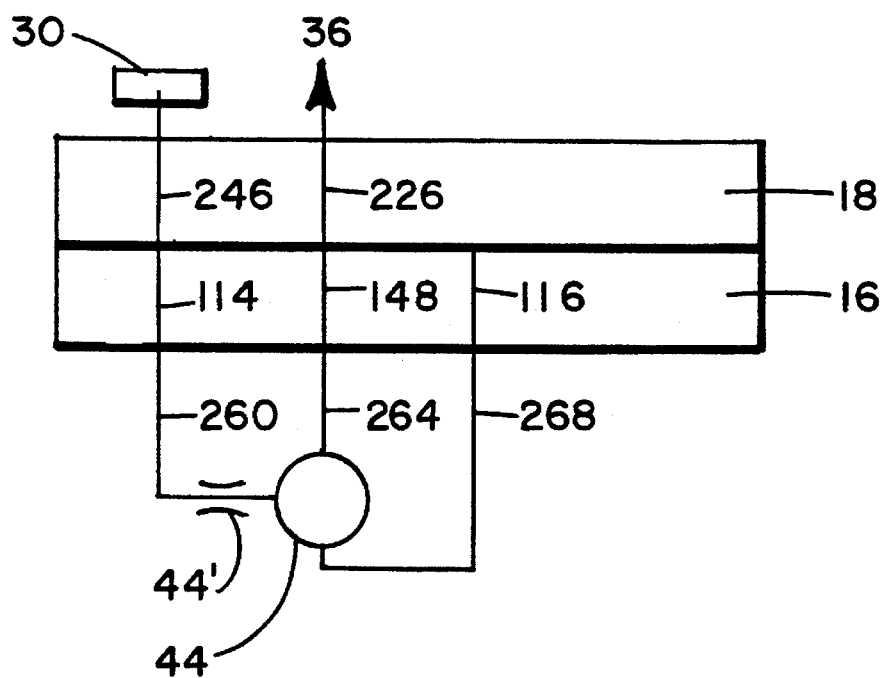

The next two steps of the operational cycle, represented in FIGS. 20 and 21, are believed optional. These steps involve the backflushing of mixing vessels 42 and 44 and including the Coulter sensing apertures 41' and 44'. Use of such backflushing steps is suggested, say at the end of a day's run and prior to shut-down. Referring to FIG. 20, the rotor 16 has been translated from its condition illustrated in FIG. 19, a further 7.5 degrees to reach a position 97.5 degrees from the initial condition thereof and assumes the thirteenth stage of the operational cycle, rotor passageways 108 and 110 are aligned with stator passageways 244 and 236 respectively. Rotor passageway 112 is blocked at its inner end within the valve assembly by surface 18" of stator 18. Passageways 142 and 222 are aligned° Vacuum is drawn on stator passageway 236 causing cleaning reagent to be drawn from source 30 into passageway 244 and passed through passageway 108 through conduit 250 to and through the Coulter sensing aperture 42' into the mixing vessel 42, to and through passageway 110 and stator passageway 236 to be directed to waste. Simultaneously, vacuum also is drawn on both rotor passageway 142 and stator passageway 222 causing their contents to be drawn to waste. Thus the mixing vessel 42 and its associated Coulter sensing aperture 42' as well as the transmission passageways 108 and 110 are backflushed and cleaned. As mentioned, some pressure may be employed during the backflushing and cleaning steps.

The rotor 16 next is translated a further 7.5 degrees to reach a condition 105.0 degrees from the initial condition of said rotor whereby to reach the fourteenth and final stage in a single full operational cycle of the valve assembly 14, said fourteenth stage being represented in FIG. 21. Stator passageway 246 is aligned with rotor passageway 114. Rotor passageway 148 is aligned with stator passageway 226 while rotor passageway 116 is blocked interior of the valve assembly 14 by the surface 18" of stator 18. Stator passageway 246 is coupled to a source of cleaner 30 of cleaner reagent. Vacuum is drawn on stator passageway 226, causing cleaner reagent to be drawn into stator passageway 246, through rotor passageway 114, then through conduit 260 to and through the Coulter sensing aperture 44' into the mixing vessel 44 and from said mixing vessel 44 via conduit 264 to the rotor passageway 148 to and through passageway 226 to waste. Thus, the operational cycle is completed with the Coulter sensing aperture 44' and the mixing vessel 44 associated therewith as well as the paths leading to and from same have been backflushed with cleaner reagent, and readied for initiating the operational cycle with a new blood sample. The rotor 16 is returned to its initial condition by rotation, preferably in the opposite direction from that employed in the steps heretofore described.

The use of the term "mixing vessels" in the course of the ensuing description is synonomous with both the "mixing and testing vessels" and "testing location" in instances when the said vessels are both present as one vessel or separate communicatively coupled vessels, the location of such vessel or vessels being referred to as a "testing location" because either one or the other or both of these vessels are present thereat.

A modified embodiment of the invention is illustrated in FIG. 22 and is designated generally by reference character 10'. The system 10' is substantially of the same construction as system 10 and employs a valve assembly 14' differing from valve assembly 14 in that the rotor 16 is superposed axially aligned with and on stator 18. The relationship of the plurality of passageways of the rotor and the stator is the same as earlier described. The valve assembly 14' is mounted on support stand 12' which includes housing 48 comprising a base plate 46' and a generally cylindrical restraining cup 48" secured to the plate 46' and having vertical wall 48'. The stand 12' is supported on legs 12" having feet 12"'. The stepper motor 50 is coupled to stepper motor gear 50' with the assembled valve assembly 14' seated on the motor shaft extender 52 coupled to the motor shaft 54. The rotor 16A and stator 18A are assembled with the rotor coaxial with the stator and the surfaces 16A" and 18A' frictionally sealably engaged. The rotor 16A is fastened to the shaft extender 52 by pin 57'. The base plate 46' includes a hollow hub formation 56' for accommodating the motor shaft 54' and extender 52'. Alignment bearing 51 is seated within the hub formation 56'. The valve assembly 14 is secured in place by retainer nut 58' and stator 18A biased against said rotor 16A by compression spring 60', retained in position properly centered coaxial with stator 18A by shaft position nut 62'. The gimballed mounting arrangement 64' comprises a pair of diametrically oppositely positioned pins 66' for supporting the stator 18A and pin 57' coupling the rotor to the shaft extender 52'. A passageway 55' is formed radially in the circumferential surface 16A''' of rotor 16A for receipt of pin 55, said pin extending outwardly of the circumferential surface 16A'''. Optically responsive switch 68' is provided for sensing pin 55 to assure the rotor 16A is positioned at the initiate position at the beginning of the operational cycle. A pair of through passageways 67.67' are formed at diametrically opposite locations near the rim of wall 48' of the cup 48" which defines the housing 48 with plate 46'. Pins 66,66" are received within said passageways 67,67'. Thus the rotor 16A and stator 18A making up the valve assembly 14' are gimbal mounted to the driving means comprising the stepper motor 50, its gear assembly 50' its shaft 54 and shaft extender 52. In all other aspects, the rotor and stator of the two embodiments have the same construction and arrangement of through passageways.

It should be understood that many variations of construction and arrangement, including numbers of through passageways and loops, and changes in the order, position, and sequence, as well as the angular rotation distances of the movable valve element during the stages of the operations described above can be made without departing from the spirit and scope of the invention as claimed hereinafter. Likewise, the volumes metered are variable from valve assembly to valve assembly depending upon the system and purpose of the system in which they are installed. The volumes are determined by the inner diameter of the pertinent passageways and the thickness of the valve element at their location, as well as the inner diameter and length of the loops employed. Other volumetric storage means can be provided in substitution for the unusually long loop portions such as the spiral portions described herein without departing from the spirit and scope of the invention as claimed herein.

What is claimed is:

1. A sampling, metering and transfer valve assembly comprising at least a pair of valve disc elements capable of being coaxially arranged, one being a rotor and the other being a stator, said valve disc elements having flat facing surfaces assembled in frictional, sealed engagement, each valve element having plural axially parallel passageways formed therethrough capable respectively for successive selected placement in communication to establish plural dedicated flow paths within the valve assembly for accommodating respectively plural different liquid bodies therein, rotation of said rotor selectively isolating precise volume aliquot portions of said different liquid bodies respectively, storing said aliquot portions of each of said different liquid bodies within said valve assembly for later retrieval, and delivering said stored aliquot portions to predetermined respective testing locations, each of said dedicated flow paths having an entry and an outlet, drive means comprising a balanced gimballed mounting for maintaining said facing surfaces sealingly engaged with the alignment of the junctures of said plural axially parallel passageways being maintained notwithstanding the exercise of rotary force upon said surfaces tending to misalign said passageways during successive rotations of said rotor whereby to maintain the continuity and integrity of said plural dedicated flow paths.

2. The valve assembly according to claim 1 and a source of differential pressure, means for coupling said source of differential pressure to the respective flow paths for moving selectively said liquid bodies along said flow paths during operation of said valve assembly.

3. The valve assembly according to claim 1 and a source of reduced pressure, means for coupling said source of reduced pressure to the respective outlets of said flow paths for moving selectively said liquid bodies along said flow paths during operation of said valve assembly.

4. The valve assembly according to any one of claims 1, 2 or 3 in which said plural dedicated flow paths are independent of each other.

5. The valve assembly according to any one of claims 1, 2 or 3 in which said plural flow paths constitute independent, dedicated flow paths each adapted to be traversed by only one type of liquid body respectively.

6. The valve assembly according to claim 1 in which said plural axially parallel passageways which define said plural dedicated flow paths include first and second measuring passageway sets arranged in serial communication for defining a continuous body of liquid sample introduced therein, said rotor being translatable to isolate aliquots of liquid sample from said continuous body and to store same within said first and second passageway sets, respectively; third and fourth measuring passageway sets arranged in serial communication for defining a continuous body of liquid diluent introduced therein, said rotor being translatable to isolate aliquots of liquid diluent and store said aliquots within each of said third and fourth measuring passageways sets, respectively; and a firth measuring passageway set for defining a continuous body of liquid reactive reagent therein, said rotor being translatable to isolate and to store an aliquot of liquid reactive reagent within said fifth measuring passageway set; circulating passageways within said valve assembly defining, along with said measuring passageway sets, dedicated flow paths through said valve assembly respectively, said measuring passageway sets and said circulating passageways including selected ones of said plural axially parallel passageways; each of said aliquots, respectively, being deliverable along the dedicated flow paths within said valve assembly to said respective testing locations, a source of reduced pressure, said delivery being effected along said dedicated flow paths under reduced pressure applied to the outlets of said dedicated passageways, the opposite ends of said dedicated flow paths defining trailing ends of said dedicated flow paths and said trailing ends being open to ambient atmosphere.

7. The valve assembly according to any one of claims 1, 2 or 3 in which one of said liquid bodies is a reactive reagent.

8. The valve assembly according to any one of claims 1 2 or 3 in which one of said liquid bodies is a lysing agent.

9. The valve assembly according to claim 1 including first and second measuring passageway sets arranged in serial communication for defining a continuous body of liquid sample introduced therein, said rotor being translatable to isolate aliquots of liquid sample from said continuous body and to store same within said first and second passageway sets respectively; third and fourth measuring passageway sets arranged in serial communication for defining a continuous body of liquid diluent introduced therein, said rotor being translatable to isolate aliquots of liquid diluent and to store said aliquots within each of said third and fourth measuring passageway sets, respectively; and a fifth measuring passageway set for defining a continuous body of liquid reactive reagent therein, said rotor being translatable to isolate and to store an aliquot of liquid reactive reagent within said fifth measuring passageway set; circulating passageways within said valve assembly and feed passageways within said valve assembly defining, along with said measuring passageway sets, said dedicated flow paths through said valve assembly, respectively, said measuring passageway sets, said circulating passageways and said feed passageways including selected ones of said plural axially parallel passageways; each of said aliquots, respectively, being deliverable along said dedicated flow paths within said valve assembly to said respective testing locations, a source of reduced pressure, movement of liquids being effected along said dedicated flow paths under reduced pressure applied to the outlets of said dedicated passageways, the opposite ends of said dedicated flow paths defining trailing ends of the liquid within said dedicated flow paths a source of pressurized inert gaseous fluid, selected ones of said trailing ends being coupled to said source of pressurized inert gaseous fluid for moving said respective liquids along said respective dedicated flow paths.

10. The valve assembly according to claim 1 including first and second passageway sets arrangeable in serial communication for defining a continuous body of liquid sample introduced therein, said rotor being translatable to isolate aliquots of liquid sample from said continuous body and to store same within said first and second passageway sets, respectively; third and fourth measuring passageway sets arrangeable in serial communication for defining a continuous body of liquid diluent introduced therein, said rotor being translatable to isolate aliquots of liquid diluent and to store said aliquots within each of said third and fourth passageway sets, respectively; and a first measuring passageway set for defining a continuous body of liquid reactive reagent within said first measuring passageway set; circulating passageways and feed passageways within said valve assembly defining, along with said measuring passageway sets, said dedicated flow paths through said valve assembly, respectively, said measuring passageways, said circulating passageways and said feed passageways including selected ones of said plural axially parallel passageways; each of said aliquots, respectively, being deliverable along said dedicated flow paths within said valve assembly to said respective testing locations, a source of reduced pressure, movement of liquids beings effected along said dedicated flow paths under reduced pressure applied to the outlets of said dedicated flow paths, the opposite ends of said dedicated flow paths defining trailing ends of said liquids within said dedicated flow paths a source of pressurized air, selected ones of said trailing ends being coupled to said source of pressurized air for supplementing the effect of said reduced pressure in moving the respective liquids to said respective testing locations.

11. The valve assembly according to claim 1 including first and second measuring passageway sets arranged in serial communication for defining a continuous body of liquid sample introduced therein, said rotor being translatable to isolate aliquots of liquid sample from said continuous body and to store same within said first and second passageway sets, respectively; third and fourth measuring passageway sets arranged in serial communication for defining a continuous body of liquid diluent introduced therein, said rotor being translatable to isolate aliquots of liquid diluent and store said aliquots within each of said third and fourth measuring passageway sets, respectively; and a fifth measuring passageway set for defining a continuous body of liquid reactive reagent therein, said rotor being translatable to isolate and to store an aliquot of liquid reactive reagent within said fifth measuring passageway set; circulating passageways within said valve assembly defining, along with said measuring passageway sets, said dedicated flow paths through said valve assembly, respectively; said measuring passageway sets and said circulating passageways including selected ones of said plural axially parallel passageways; each of said aliquots, respectively, being deliverable along the dedicated flow paths within said valve assembly to said respective testing locations, a source of reduced pressure, said delivery being effected under reduced pressure applied to the outlets of said dedicated flow paths, the opposite ends of said dedicated flow paths defining trailing ends of the liquids within said dedicated flow paths, a source of pressurized air, selected ones of said trailing end portions being coupled to said source of pressurized air for application thereof thereto simultaneously during application of reduced pressure to the outlets of said dedicated flow paths.

12. The valve assembly according to any one of claims 1, 2 or 3 in which there is provided a source of gaseous fluid pressure, means coupling said source of gaseous fluid pressure to the respective testing locations for introduction of gaseous fluid pressure to said testing locations subsequent to delivery thereto of said selected ones of said aliquots for mixing of said aliquots.

13. The valve assembly according to any one of claims 1, 2 or 3 in which there is provided a source of gaseous fluid pressure, means coupling said source of gaseous fluid pressure to the respective testing locations for introduction of said gaseous fluid pressure in pulsed delivery to said testing locations by way of said valve assembly subsequent to delivery thereto of selected ones of said aliquots for mixing said aliquots.

14. The valve assembly according to claim 1 and a source of reduced pressure, said reduced pressure being applied in pulses to the testing locations immediately subsequent to delivery of said aliquots of liquid diluent and said aliquots of liquid reactive reagent respectively thereto, whereby to introduce air as mixing bubbles thereinto.

15. The valve assembly according to any one of claims 1, 2 or 3 and programmable control means coupled to said drive means for effecting selective step by step rotation of said rotor coordinated to effect the introduction of said respective liquids, isolation and storage of said respective aliquots and delivery of said respective aliquots to the respective locations in a predetermined order of occurrence.

16. The valve assembly according to any one of claims 1 2 or 3 and programmable control means governing translation of said rotor in accordance with a predetermined step by step operational pattern and further including sensing means at said testing locations providing data for determining selected characteristics of said liquid sample.

17. The valve assembly according to any one of claims 1, 2 or 3 in which selected ones of said parallel passageways are linked by hollow externally extending loops having precise interior volumes, respectively, for forming said respective aliquots of said respective liquids, isolating and storing said aliquots respectively therein for later retrieval.

18. The valve assembly according to any one of claims 1, or 2 and a housing for accommodating said valve assembly, said balanced gimballed mounting comprising first means defining a pivot axis, said drive means including a driven shaft and means coupling the axial portion of said rotor to said driven shaft, said coupling means lying along a line 180 degrees angularly spaced from said first pivot axis defining a second pivot axis, said stator having limited freedom of movement about said first pivot axis and said rotor having limited freedom of movement about said second pivot axis to permit inclination of said stator to effect compensatory identical inclination of said rotor and stator facing surfaces during relative rotation of said rotor and stator.

19. The valve assembly according to any one of claims 1, 2 or 3 and a housing for accommodating said valve assembly, said balanced gimballed mounting comprising first pin means secured at diametrically opposed locations of the outer circumference of said stator and said first pin means being coupled to said housing defining a first pivot axis extending through said first pin means, said stator and rotor each having a coaxial center passageway, said drive means including a driven shaft arranged to pass through said center passageways and means coupling the axial portion of said rotor to said driven shaft, said last mentioned coupling means defining a second pivot axis lying along a line 180 degrees angularly spaced from said first pivot axis and said rotor has limited freedom of movement about said second pivot axis to permit inclination of said stator to effect compensatory identical inclination of said rotor and stator facing surfaces during relative motion of said rotor and stator.

20. The valve assembly according to claim 1 and a source of differential pressure; and further, there being plural measuring passageway sets including selected pairs of said plural axially parallel passageways formed in said valve disc elements, each measuring passageway set including a hollow, outwardly extending loop linkage therebetween to define a measuring chamber having a precise interior volume; selected ones of others of said plural axially parallel passageways defining circulating passageways and feed passageways within said valve disc elements; relative rotation of said rotor and stator isolating said precise volume aliquots of the respective different liquid bodies within respective measuring chambers for temporary storage therein; said measuring, circulating and feed passageways defining said plural dedicated flow paths respectively distinct for each of said different liquid bodies, each of said dedicated flow paths handling only one type of liquid, respectively; all metering, isolating, storing and delivery of said precise volume aliquots being effected within said valve assembly; further rotation of said rotor enabling passage of said respective aliquots along respective dedicated flow paths under the influence of said differential pressure to said testing locations.

21. The valve assembly according to claim 1 and a source of differential pressure; and further, there being plural measuring passageway sets including selected pairs of said axially parallel passageways formed in said valve elements, each measuring passageway set including a hollow outwardly extending look linkage therebetween to define a measuring chamber having a precise volume; selected ones of others of said plural axially parallel passageways defining respectively, circulating passageways and feed passageways within said valve assembly, said circulating passageways and feed passageways, with said measuring passageway sets, defining said plural dedicated flow paths, rotation of said rotor relative said stator isolating said precise volume aliquots of the respective liquid bodies within said measuring chambers for temporary storage therein and later retrieval thereof, all liquid metering, isolating, storing and delivery of said precise volume aliquots being effected within said valve assembly, movement of said respective liquids and aliquots thereof along said dedicated flow paths being effected under the influence of said differential pressure respectively.

22. The valve assembly according to claim 21 in which said source of differential pressure includes a vacuum source, means coupling said vacuum source to the outlets of selected ones of said dedicated flow paths, vacuum being applied during the introduction of said respective different liquids to said respective flow paths.

23. In apparatus for ascertaining a plurality of parameters of biological liquid samples such as blood, said apparatus including respective sources of diluent and reactive reagent, at least a pair of testing chambers including mixing and sensing portions, the sensing portion including fine aperture sensing means and electrode means providing an independent scanning circuit for obtaining signals arising from the passing of a portion of the sample through the restricted current field defined within the fine aperture sensing means, means for electrically detecting the respective signals produced by the scanning circuits and deriving therefrom a plurality of electrical pulses whose amplitude respectively is proportional to selected characteristics of the biological liquid sample passing through said fine aperture sensing means, means for deriving separate accumulated values respectively of the number of pulses produced in the respective detecting means, means for computing, storing and displaying data representative of each of the plurality of parameters of said biological liquid samples; the improvement comprising, a multifunctional sampling, metering and transfer valve assembly for performing all the fluid handling functions within the valve assembly to meter, to isolate, to store for later retrieval and to deliver precise volume aliquots of liquid sample, of diluent and of reactive reagent respectively from sources thereof to respective testing chambers, said valve assembly formed of at lest a pair of coaxially disposed valve disc elements superposed and arranged engaged in frictional, sealed face to face surface engagement, one of said valve disc elements constituting a rotor and the other of said valve disc elements having a plurality of axially parallel through passageways, selected pairs of said passageways being linked by a hollow outwardly extending loop, each pair of said passageways together with the loop defining a measuring chamber, selected other ones of said passageways also comprising circulating passageways and feed passageways together with respective measuring chambers defining plural dedicated flow paths, each having an inlet and an outlet and each adapted to contain only one type of liquid, respectively, said rotor being stepwise rotationally translatable relative to said stator in accordance with a preprogrammed order, preprogrammed control means for effecting operation of said valve assembly in accordance with said order, each of said dedicated flow paths capable of receiving a respective one of plural independent continuous bodies of said liquid sample, of liquid diluent and of liquid reactive reagent, rotary translation of said rotor effecting the metering, isolating and storing for later retrieval, respectively, of precise volume aliquots of each of said continuous liquid bodies within said respective measuring chambers, all metering, isolating and storing of said aliquot volumes being effected within said valve assembly, means for delivering each of said aliquots to said testing chambers along said respective dedicated flow paths, there being a source of differential pressure and said delivery being effected under the influence of said differential pressure, drive means for effecting step by step translating of said rotor relative to said stator, and means mounting said valve assembly to said drive means and means preventing misalignment of said passageways at the junctures thereof notwithstanding the vectorial forces tending to be caused by the rotational force exercised upon the facing frictionally sealingly engaged surfaces during the translation of said rotor relative to said stator while the valve assembly is in operation and the rotor is moving, and said mounting means comprise a balanced gimballed mounting arrangement coupling said valve assembly to the drive means therefor.

24. The apparatus of claim 23 wherein said reactive reagent is a lysing agent.

25. The apparatus according to claims 23 or 24 in which said mounting means comprise a gimballed mounting arrangement capable of maintaining the rotor and stator in face to face sealed frictional engagement yet permitting limited relative freedom of movement of said rotor and stator whereby inclination of one of said rotor and stator will be compensated by identical inclination of the other of said rotor and stator following said one element during relative rotation whereby frictional engagement and alignment of said rotor and stator is maintained.

26. The apparatus according to claims 23 or 24 in which said mounting means comprise a balanced gimballed mounting having support means for the valve assembly, first pin and slot means carried by said support means and said stator at diametrically opposed locations thereon, second pin and slot means carried by said rotor and said drive means, said second pin and slot means located along a line taken 180 degrees from a line taken through the first pin and slot means, whereby the stator is gimballed at the circumference thereof and the rotor is gimballed at the center thereof thereby defining a four point balanced gimballed coupling relationship of the valve assembly to the drive means.

27. A sampling, metering and transfer valve assembly comprising at least a pair of valve disc members coaxially arranged, at least one being a rotor, said valve disc members having flat facing surfaces assembled in frictional sealed engagement, each valve disc member having plural axially parallel through passageways located respectively for successive selective placement in communication to establish plural dedicated flow paths within said valve assembly for accommodating respectively plural different independent continuous bodies of respectively different types of liquids therein from sources thereof, said rotor being rotatable selectively successively for metering, isolating and storing for later retrieval precise volume aliquot portions of each of said respective different liquid bodies within said valve assembly and delivering said stored aliquot portions to a testing chamber as a series of successive operations, respectively, each of said plural dedicated flow paths receiving only one type of liquid, respectively, all metering, isolating, storing and delivery of said aliquot volumes being effected within said valve assembly, each of said dedicated flow paths having an inlet and an outlet, means coupling said outlets respectively to said testing chamber, and means maintaining said frictionally engaged faces of said valve disc members in sealed frictional engagement notwithstanding the exercise of vectorial force effects upon the facing surfaces of said valve disc members tending to arise during successive rotation of said rotor while the valve assembly is operating said means comprising providing a source of less than atmospheric pressure, means coupling said source of less than atmospheric pressure selectively to the respective outlets of said dedicated flow paths, maintaining the respective inlets of said dedicated flow paths selectively open to the ambient atmosphere whereby to enable air to be drawn therein while the less than atmospheric pressure is drawn on the respective outlet for moving liquid through said dedicated flow paths respectively, and drive means for step-by-step rotation of said rotor and said maintaining means additionally include a balanced gimbal mounting of the rotor coupling said rotor to said drive means and maintaining the axially parallel through passageways against misalignment at their junctures.

28. The valve assembly according to claim 27 in which there is provided a source of gaseous fluid pressure greater than atmospheric pressure and means for coupling said source of gaseous fluid pressure greater than atmospheric pressure to the inlets of selected dedicated flow paths for aiding in effecting delivery to said testing locations.

29. The valve assembly according to claim 27 wherein said axially parallel through passageways include first and second measuring passageways formed in said valve disc members and hollow outwardly extending loops linking said first and second measuring passageways and arranged in serial communication respectively to define one of said dedicated flow paths for receiving a continuous body of liquid sample introduced therein from a source thereof, said rotor being translatable to segment said continuous body of liquid sample whereby to meter, isolate and gore for later retrieval precise volume aliquots of liquid sample within said valve assembly, other of said axially parallel through passageways include third and fourth measuring passageways formed in said valve disc members and second hollow loops linking said third and fourth measuring passageways arranged in serial communication for defining a second dedicated flow path for receiving a continuous body of liquid diluent introduced therein from a source thereof, translation of said rotor segmenting said continuous body of liquid diluent meter& isolating and storing for later retrieval precise volume aliquots of said liquid diluent within said valve assembly, said plural axially parallel passageways further including fifth and sixth measuring passageways formed in said valve disc members arranged in serial communication and a third hollow loop linking said fifth and sixth passageways to define a third dedicated flow path for receiving a continuous body of liquid lysing reagent introduced therein from a source thereof, translation of said rotor segmenting said continuous body of liquid lysing reagent isolating and storing for later retrieval a precise volume aliquot of said liquid lysing reagent within said valve assembly, said plural axially parallel passageways including cooperating circulating passageways arranged in communication with respective ones of said aliquot portions said plural axially parallel passageways additionally including feed passageways arranged capable of being coupled to said respective sources, respectively, and together further defining said dedicated flow paths, respectively, said means for moving said liquids along respective dedicated flow paths comprising said source of lower than atmospheric pressure for pulling the respective liquids along the respective dedicated flow paths.

30. A multifunctional sampling, metering and transfer valve assembly for use in a particle study system and capable of performing all required liquid handling functions within said valve assembly to provide metered, isolated and stored precise volume aliquots of liquid sample, of liquid diluent and of liquid reagent, respectively, within said valve assembly for delivery to predetermined testing chambers in accordance with a preprogrammed order of operation, said valve assembly comprising at least a pair of valve disc elements arranged superposed and having facing surfaces frictionally sealably engaged, one of said pair of valve disc elements being a rotor and the other of said pair of valve disc elements being a stator, said rotor and stator each having plural through, axially parallel passageways of precise internal volume selectively alignable, said rotor being selectively and successively angularly rotationally translatable stepwise relative to said stator to place selected ones of said passageways as sets in communication, each passageway set being linked by a hollow, outwardly extending loop of precise internal volume defining measuring chambers, there being additionally, plural cooperating axially parallel feed passageways and plural cooperating axially parallel circulating passageways, said passageways adapted to define plural non-interferant dedicated liquid flow paths through said valve assembly, each of said flow paths receiving only one of type of said liquids, all metering, isolating, storing and delivery of said respective liquids being effected within said valve assembly, each of said liquid flow paths having an entry and an outlet, drive means adapted to be coupled to said rotor and stator in assembly for step-wise translation of said rotor and means maintaining said assembly in face to face aligned frictional sealed engagement notwithstanding the tendency of the rotational forces to effect misalignment of said passageways at their junctures during rotation of said rotor whereby to prevent leakage and prevent misalignment of said passageways at their junctures said maintaining means include means defining a balanced gimballed mounting coupling said drive means to said valve assembly maintaining said frictional sealed engagement during rotation of said rotor yet permitting limited relative freedom of movement of said valve disc elements whereby inclination of one of said elements will be compensated by identical following inclination of the other of said elements so that vectorial misalignment of the junctions of said passageways at the facing surfaces of said elements is prevented during operation of said valve assembly.

31. The valve assembly according to claim 30 wherein there is a source of reduced pressure and said maintaining means includes means coupling the respective outlets to the source of reduced pressure for drawing reduced pressure on said outlets effecting movement of said liquids through said dedicated flow paths.

32. The valve assembly according to claim 30 in which air is permitted to flow into the inlets of said dedicated flow paths while less than atmospheric pressure is applied at the outlets thereof.

* * * * *